US009198742B2

(12) United States Patent
Marks et al.

(10) Patent No.: US 9,198,742 B2
(45) Date of Patent: *Dec. 1, 2015

(54) IMPLANT SURFACE WITH INCREASED HYDROPHILICITY

(71) Applicant: Biomet 3i, LLC, Palm Beach Gardens, FL (US)

(72) Inventors: Jacqueline K. Marks, Jupiter, FL (US); Robert L. Mayfield, Jupiter, FL (US); Ross W. Towse, Fort Wayne, IN (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/470,915

(22) Filed: Aug. 27, 2014

(65) Prior Publication Data

US 2014/0370461 A1 Dec. 18, 2014

Related U.S. Application Data

(63) Continuation of application No. 13/648,837, filed on Oct. 10, 2012, now Pat. No. 8,852,672, which is a continuation of application No. 12/359,780, filed on Jan. 26, 2009, now Pat. No. 8,309,162.

(60) Provisional application No. 61/137,293, filed on Jul. 28, 2008, provisional application No. 61/062,577, filed on Jan. 28, 2008.

(51) Int. Cl.
| | |
|---|---|
| A61C 8/00 | (2006.01) |
| A61L 27/28 | (2006.01) |
| A61L 27/38 | (2006.01) |
| A61L 27/06 | (2006.01) |
| A61L 27/10 | (2006.01) |
| A61L 27/32 | (2006.01) |
| A61L 27/50 | (2006.01) |
| A61K 6/02 | (2006.01) |
| A61K 6/04 | (2006.01) |
| A61L 27/30 | (2006.01) |
| C23F 1/30 | (2006.01) |

(52) U.S. Cl.
CPC .............. *A61C 8/0013* (2013.01); *A61C 8/005* (2013.01); *A61C 8/0012* (2013.01); *A61C 8/0022* (2013.01); *A61K 6/0205* (2013.01); *A61K 6/04* (2013.01); *A61L 27/06* (2013.01); *A61L 27/10* (2013.01); *A61L 27/306* (2013.01); *A61L 27/32* (2013.01); *A61L 27/50* (2013.01); *C23F 1/30* (2013.01); *A61C 8/006* (2013.01); *A61L 2400/18* (2013.01); *A61L 2430/12* (2013.01)

(58) Field of Classification Search
USPC ............ 427/2.24, 2.25, 2.26, 2.27; 433/201.1
See application file for complete search history.

(56) References Cited

U.S. PATENT DOCUMENTS

| | | |
|---|---|---|
| 3,772,355 A | 11/1973 | Merz |
| 3,984,914 A | 10/1976 | Schwartz |
| 4,097,935 A | 7/1978 | Jarcho |
| 4,131,597 A | 12/1978 | Bluethgen et al. |
| 4,145,764 A | 3/1979 | Suzuki et al. |
| 4,146,936 A | 4/1979 | Aoyagi et al. |
| 4,223,412 A | 9/1980 | Aoyagi et al. |
| 4,321,042 A | 3/1982 | Scheicher |
| 4,330,891 A | 5/1982 | Branemark et al. |
| 4,366,183 A | 12/1982 | Ghommidh et al. |
| 4,403,941 A | 9/1983 | Okiura et al. |
| 4,451,235 A | 5/1984 | Okuda et al. |
| 4,538,306 A | 9/1985 | Dorre et al. |
| 4,636,526 A | 1/1987 | Dorman et al. |
| 4,687,487 A | 8/1987 | Hintermann |
| 4,746,532 A | 5/1988 | Suzuki et al. |
| 4,818,559 A | 4/1989 | Hama et al. |
| 4,830,993 A | 5/1989 | Legrand et al. |
| 4,846,837 A | 7/1989 | Kurze et al. |
| 4,847,163 A | 7/1989 | Shimamune et al. |
| 4,863,474 A | 9/1989 | Brown et al. |
| 4,871,578 A | 10/1989 | Adam et al. |
| 4,879,136 A | 11/1989 | Polz |
| 4,880,610 A | 11/1989 | Constantz |
| 4,882,196 A | 11/1989 | Shimamune et al. |
| 4,904,534 A | 2/1990 | Nagai |
| 4,908,030 A | 3/1990 | Linkow et al. |
| 4,909,846 A | 3/1990 | Barfurth et al. |
| 4,911,953 A | 3/1990 | Hosonuma et al. |
| 4,929,589 A | 5/1990 | Martin et al. |
| 4,944,754 A | 7/1990 | Linkow et al. |

(Continued)

FOREIGN PATENT DOCUMENTS

| | | |
|---|---|---|
| DE | 3516411 | 11/1986 |
| EP | 0388576 | 11/1989 |

(Continued)

OTHER PUBLICATIONS

Baier, *The Role of Surface Energy in Thrombogenesis*, Bull N.Y. Acad. Med., Feb. 1972 pp. 257-272, vol. 48, No. 2, Buffalo, N.Y., U.S.A.

Boehm, *Acidic and Basic Properties of Hydroxylated Metal Oxide Surfaces*, Discussions Faraday Society, pp. 264-275, No. 52, Munchen, Germany (1971).

Cleries et al., *Dissolutino Behaviour of Calcium Phosphate Coatings Obtained by Laser Ablation*, Biomaterials, 1998 pp. 1483-1487, vol. 19, No. 16, Elsevier Science Publishers BV, Barking, GB.

International Search Report, PCT-US09-31771, Date of mailing Mar. 3, 2009, 2 pages.

International Written Opinion, PCT-US09-31771, Date of mailing Mar. 3, 2009, 6 pages.

(Continued)

*Primary Examiner* — Michael J Feely

(74) *Attorney, Agent, or Firm* — Nixon Peabody LLP

(57) ABSTRACT

A method of increasing the hydrophilicity of an implant to be implanted into living bone. The method comprises the act of depositing non-toxic salt residuals on the surface of the implant by exposing the surface to a solution including the non-toxic salts. The method further comprises the act of drying the implant.

20 Claims, 21 Drawing Sheets

(56) References Cited

U.S. PATENT DOCUMENTS

| | | |
|---|---|---|
| 4,960,646 A | 10/1990 | Shimamune et al. |
| 4,965,088 A | 10/1990 | Shimamune et al. |
| 4,969,906 A | 11/1990 | Kronman |
| 4,988,362 A | 1/1991 | Toriyama et al. |
| 4,990,163 A | 2/1991 | Ducheyne et al. |
| 5,030,474 A | 7/1991 | Saita et al. |
| 5,068,122 A | 11/1991 | Kokubo et al. |
| 5,071,434 A | 12/1991 | Tsuzuki et al. |
| 5,071,436 A | 12/1991 | Huc et al. |
| 5,077,132 A | 12/1991 | Maruno et al. |
| 5,092,890 A | 3/1992 | Pohlemann et al. |
| 5,128,169 A | 7/1992 | Saita et al. |
| 5,134,009 A | 7/1992 | Ichitsuka et al. |
| 5,141,576 A | 8/1992 | Shimamune et al. |
| 5,180,426 A | 1/1993 | Sumita |
| 5,185,208 A | 2/1993 | Yamashita et al. |
| 5,188,670 A | 2/1993 | Constantz |
| 5,196,201 A | 3/1993 | Larsson et al. |
| 5,205,921 A | 4/1993 | Shirkanzadeh |
| 5,207,705 A | 5/1993 | Trudell et al. |
| 5,219,361 A | 6/1993 | von Recum et al. |
| 5,231,151 A | 7/1993 | Spencer et al. |
| 5,263,491 A | 11/1993 | Thornton |
| 5,279,720 A | 1/1994 | Divigalpitiya |
| 5,279,831 A | 1/1994 | Constantz et al. |
| 5,286,571 A | 2/1994 | Mirkin et al. |
| 5,344,457 A | 9/1994 | Pilliar et al. |
| 5,344,654 A | 9/1994 | Rueger et al. |
| 5,358,529 A | 10/1994 | Davidson |
| 5,397,642 A | 3/1995 | Li et al. |
| 5,456,723 A | 10/1995 | Steinemann et al. |
| 5,478,237 A | 12/1995 | Ishizawa |
| 5,484,286 A | 1/1996 | Hansson |
| 5,501,706 A | 3/1996 | Arenberg |
| 5,522,893 A | 6/1996 | Chow et al. |
| 5,527,837 A | 6/1996 | Kondou et al. |
| 5,543,019 A | 8/1996 | Lee et al. |
| 5,558,517 A | 9/1996 | Shalaby et al. |
| 5,571,188 A | 11/1996 | Ellingsen et al. |
| 5,584,875 A | 12/1996 | Duhamel et al. |
| 5,603,338 A | 2/1997 | Beaty |
| 5,609,633 A | 3/1997 | Kokubo |
| 5,612,049 A | 3/1997 | Li et al. |
| 5,639,402 A | 6/1997 | Barlow et al. |
| 5,652,016 A | 7/1997 | Imura et al. |
| 5,683,249 A | 11/1997 | Ibsen et al. |
| 5,700,289 A | 12/1997 | Breitbart et al. |
| 5,722,439 A | 3/1998 | Endelson |
| 5,726,524 A | 3/1998 | Debe |
| 5,727,943 A | 3/1998 | Beaty et al. |
| 5,730,598 A | 3/1998 | Story et al. |
| 5,733,564 A | 3/1998 | Lehtinen |
| 5,759,376 A | 6/1998 | Teller et al. |
| 5,759,598 A | 6/1998 | Gaier |
| 5,763,092 A | 6/1998 | Lee et al. |
| 5,766,247 A | 6/1998 | Aoki et al. |
| 5,766,669 A | 6/1998 | Pugh et al. |
| 5,767,032 A | 6/1998 | Hokkanen et al. |
| 5,772,439 A | 6/1998 | Yamaoka et al. |
| 5,807,430 A | 9/1998 | Zheng et al. |
| 5,811,151 A | 9/1998 | Hendriks et al. |
| 5,817,326 A | 10/1998 | Nastasi et al. |
| 5,820,368 A | 10/1998 | Wolk |
| 5,858,318 A | 1/1999 | Luo |
| 5,871,547 A | 2/1999 | Abouaf et al. |
| 5,876,453 A | 3/1999 | Beaty |
| 5,902,109 A | 5/1999 | Reams et al. |
| 5,932,299 A | 8/1999 | Katoot |
| 5,934,287 A | 8/1999 | Hayashi et al. |
| 5,938,435 A | 8/1999 | Raspino, Jr. |
| 5,947,893 A | 9/1999 | Agrawal et al. |
| 5,952,399 A | 9/1999 | Rentsch |
| 5,958,340 A | 9/1999 | Meyer et al. |
| 5,958,504 A | 9/1999 | Lee et al. |
| 5,962,549 A | 10/1999 | Bonfield et al. |
| 5,981,619 A | 11/1999 | Shikinami et al. |
| 5,990,381 A | 11/1999 | Nishihara |
| 6,013,591 A | 1/2000 | Ying et al. |
| 6,051,272 A | 4/2000 | Stupp et al. |
| 6,069,295 A | 5/2000 | Leitao |
| 6,077,989 A | 6/2000 | Kanel et al. |
| 6,129,928 A | 10/2000 | Sarangapani et al. |
| 6,136,369 A | 10/2000 | Leitao et al. |
| 6,139,585 A | 10/2000 | Li |
| 6,143,037 A | 11/2000 | Goldstein et al. |
| 6,143,948 A | 11/2000 | Leitao et al. |
| 6,146,686 A | 11/2000 | Leitao |
| 6,146,767 A | 11/2000 | Schwartz |
| 6,153,266 A | 11/2000 | Yokogawa et al. |
| 6,153,664 A | 11/2000 | Wise et al. |
| 6,183,255 B1 | 2/2001 | Oshida |
| 6,190,412 B1 | 2/2001 | Lee et al. |
| 6,200,137 B1 | 3/2001 | Holand et al. |
| 6,206,598 B1 | 3/2001 | Johnson et al. |
| 6,221,111 B1 | 4/2001 | Piveteau et al. |
| 6,261,322 B1 | 7/2001 | Despres, III et al. |
| 6,270,347 B1 | 8/2001 | Webster et al. |
| 6,280,789 B1 | 8/2001 | Rey et al. |
| 6,280,863 B1 | 8/2001 | Frank et al. |
| 6,290,982 B1 | 9/2001 | Seppala et al. |
| 6,306,784 B1 | 10/2001 | Drescher et al. |
| 6,306,925 B1 | 10/2001 | Clupper et al. |
| 6,309,660 B1 | 10/2001 | Hsu et al. |
| 6,338,810 B1 | 1/2002 | Carpena et al. |
| 6,344,061 B1 | 2/2002 | Leitao et al. |
| 6,344,209 B1 | 2/2002 | Saito et al. |
| 6,344,276 B1 | 2/2002 | Lin et al. |
| 6,372,354 B1 | 4/2002 | Park et al. |
| 6,395,299 B1 | 5/2002 | Babich et al. |
| 6,399,215 B1 | 6/2002 | Zhu et al. |
| 6,419,708 B1 | 7/2002 | Hall et al. |
| 6,426,114 B1 | 7/2002 | Troczynski et al. |
| 6,428,803 B1 | 8/2002 | Ewers et al. |
| 6,508,838 B2 | 1/2003 | Lee et al. |
| 6,518,328 B2 | 2/2003 | Kumar |
| 6,527,849 B2 | 3/2003 | Dry |
| 6,530,958 B1 | 3/2003 | Cima et al. |
| 6,544,732 B1 | 4/2003 | Chee et al. |
| 6,569,292 B2 | 5/2003 | Coffer |
| 6,569,489 B1 | 5/2003 | Li |
| 6,589,590 B2 | 7/2003 | Czernuszka |
| 6,596,338 B2 | 7/2003 | Scott et al. |
| 6,617,142 B2 | 9/2003 | Keogh et al. |
| 6,620,861 B1 | 9/2003 | Nakatuka et al. |
| 6,645,644 B1 | 11/2003 | Schwartz et al. |
| 6,652,765 B1 | 11/2003 | Beaty |
| 6,740,366 B2 | 5/2004 | Hori et al. |
| 6,790,455 B2 | 9/2004 | Chu et al. |
| 6,853,075 B2 | 2/2005 | Auner et al. |
| 6,919,070 B1 | 7/2005 | Rudin et al. |
| 6,960,249 B2 | 11/2005 | Lin et al. |
| 6,969,474 B2 | 11/2005 | Beaty |
| 6,969,501 B2 | 11/2005 | Sapieszko et al. |
| 6,991,803 B2 | 1/2006 | Sapieszko et al. |
| 7,007,872 B2 | 3/2006 | Yadav et al. |
| 7,018,418 B2 | 3/2006 | Amrich et al. |
| 7,067,169 B2 | 6/2006 | Liu et al. |
| 7,067,577 B2 | 6/2006 | Aramaki et al. |
| 7,083,642 B2 | 8/2006 | Sirhan et al. |
| 7,087,086 B2 | 8/2006 | Li et al. |
| 7,105,030 B2 | 9/2006 | Despres, III et al. |
| 7,112,063 B2 | 9/2006 | Bulard et al. |
| 7,169,317 B2 | 1/2007 | Beaty |
| 7,341,756 B2 | 3/2008 | Liu et al. |
| 8,029,283 B2 | 10/2011 | Schwarz et al. |
| 8,057,843 B2 | 11/2011 | Schlottig et al. |
| 8,309,162 B2 | 11/2012 | Charlton |
| 8,641,418 B2 | 2/2014 | Mayfield et al. |
| 8,852,672 B2 * | 10/2014 | Charlton et al. ............. 427/2.27 |
| 9,034,201 B2 * | 5/2015 | Mayfield et al. ............. 216/83 |
| 2001/0020476 A1 | 9/2001 | Gan et al. |
| 2002/0016635 A1 | 2/2002 | Despres, III et al. |
| 2002/0018798 A1 | 2/2002 | Sewing et al. |
| 2002/0028424 A1 | 3/2002 | Prestipino et al. |

(56) References Cited

U.S. PATENT DOCUMENTS

| | | |
|---|---|---|
| 2002/0119325 A1 | 8/2002 | Park et al. |
| 2002/0127391 A1 | 9/2002 | Kumar |
| 2003/0005646 A1 | 1/2003 | McHale, Jr. |
| 2003/0082232 A1 | 5/2003 | Lee et al. |
| 2003/0099762 A1 | 5/2003 | Zhang et al. |
| 2003/0175773 A1 | 9/2003 | Chee et al. |
| 2003/0219466 A1 | 11/2003 | Kumta et al. |
| 2003/0219562 A1 | 11/2003 | Rypacek et al. |
| 2003/0231984 A1 | 12/2003 | Bright et al. |
| 2004/0023048 A1 | 2/2004 | Schwartz et al. |
| 2004/0024081 A1 | 2/2004 | Trieu et al. |
| 2004/0053197 A1 | 3/2004 | Minevski et al. |
| 2004/0053198 A1 | 3/2004 | Minevski et al. |
| 2004/0053199 A1 | 3/2004 | Minevski et al. |
| 2004/0083006 A1 | 4/2004 | Ellingsen et al. |
| 2004/0109937 A1 | 6/2004 | Jennissen et al. |
| 2004/0121290 A1 | 6/2004 | Minevski et al. |
| 2004/0121451 A1 | 6/2004 | Moritz et al. |
| 2004/0145053 A1 | 7/2004 | Auner et al. |
| 2004/0149586 A1 | 8/2004 | Sul |
| 2004/0210309 A1 | 10/2004 | Denzer et al. |
| 2004/0241613 A1 | 12/2004 | Jansen et al. |
| 2004/0249472 A1 | 12/2004 | Liu et al. |
| 2004/0258726 A1 | 12/2004 | Stupp et al. |
| 2004/0265780 A1 | 12/2004 | Robb et al. |
| 2005/0008620 A1 | 1/2005 | Shimp et al. |
| 2005/0014151 A1 | 1/2005 | Textor et al. |
| 2005/0019365 A1 | 1/2005 | Frauchiger et al. |
| 2005/0031704 A1 | 2/2005 | Ahn |
| 2005/0038498 A1 | 2/2005 | Dubrow et al. |
| 2005/0100937 A1 | 5/2005 | Holmes |
| 2005/0171615 A1 | 8/2005 | Georgette et al. |
| 2005/0211680 A1 | 9/2005 | Li et al. |
| 2005/0221072 A1 | 10/2005 | Dubrow et al. |
| 2005/0226939 A1 | 10/2005 | Ramalingam et al. |
| 2005/0249654 A1 | 11/2005 | Chow |
| 2006/0039951 A1 | 2/2006 | Sapieszko et al. |
| 2006/0078587 A1 | 4/2006 | Leong |
| 2006/0105015 A1 | 5/2006 | Perla et al. |
| 2006/0110306 A1 | 5/2006 | Chow et al. |
| 2006/0141002 A1 | 6/2006 | Liu et al. |
| 2006/0178751 A1 | 8/2006 | Despres, III et al. |
| 2006/0229715 A1 | 10/2006 | Istephanous et al. |
| 2006/0246105 A1 | 11/2006 | Molz et al. |
| 2006/0257358 A1 | 11/2006 | Wen et al. |
| 2006/0257492 A1 | 11/2006 | Wen et al. |
| 2007/0010893 A1 | 1/2007 | Wen et al. |
| 2007/0055254 A1 | 3/2007 | Ihde |
| 2007/0110890 A1 | 5/2007 | Berckmans, III et al. |
| 2007/0112353 A1 | 5/2007 | Berckmans et al. |
| 2007/0173952 A1 | 7/2007 | Hermansson et al. |
| 2007/0202144 A1 | 8/2007 | Hellerbrand et al. |
| 2007/0202462 A1 | 8/2007 | Schwarz et al. |
| 2007/0299535 A1 | 12/2007 | Ihde |
| 2008/0044451 A1 | 2/2008 | Steinmuller-Nethl et al. |
| 2008/0188938 A1 | 8/2008 | Gazza |
| 2009/0132048 A1 | 5/2009 | Denzer |
| 2010/0179665 A1 | 7/2010 | Schlottig et al. |
| 2011/0104638 A1 | 5/2011 | Schlottig et al. |
| 2011/0171602 A1 | 7/2011 | Schlottig et al. |
| 2011/0233169 A1 | 9/2011 | Mayfield et al. |
| 2013/0248487 A1 | 9/2013 | Mayfield et al. |
| 2014/0034606 A1 | 2/2014 | Mayfield et al. |

FOREIGN PATENT DOCUMENTS

| | | |
|---|---|---|
| EP | 0450939 | 1/1997 |
| EP | 0806212 | 11/1997 |
| EP | 0987031 | 3/2000 |
| EP | 1275422 | 1/2003 |
| EP | 1053739 B1 | 11/2005 |
| EP | 1847278 | 10/2007 |
| GB | 2045083 | 10/1980 |
| JP | 2-018463 | 1/1990 |
| JP | 05-23361 | 2/1993 |
| JP | 5-224448 | 9/1993 |
| JP | 05-228207 | 9/1993 |
| JP | 2000-327515 | 11/2000 |
| WO | WO95-13101 | 5/1995 |
| WO | WO95-13102 | 5/1995 |
| WO | WO96-39202 | 12/1996 |
| WO | WO00-44305 | 8/2000 |
| WO | WO01-37752 | 5/2001 |
| WO | WO02-03880 | 1/2002 |
| WO | WO02-20873 | 3/2002 |
| WO | WO03-030957 | 4/2003 |
| WO | WO2006-096793 | 9/2006 |
| WO | WO2006-102347 | 9/2006 |
| WO | WO2006-004778 | 12/2006 |
| WO | WO2007-001744 | 1/2007 |
| WO | WO2007-035217 | 3/2007 |
| WO | WO2007-059038 | 5/2007 |
| WO | WO2007-118734 | 10/2007 |

OTHER PUBLICATIONS

Leeuwenburgh et al., *Osteoclastic Resorption of Biomimetic Calcium Phosphate Coatings in Vitro*, Journal of Biomedical Materials Research, 2001, pp. 208-215, vol. 56, No. 2, John Wiley & Sons, Inc.

Lucke et al., *Getamicin Coating of Metallic Implants Reduces Implant-Related Osteomyelitis in Rats*, Bone. 2003, pp. 521-531, vol. 32, No. 5, Elsevier Science, New York.

\* cited by examiner

IMPLANT SURFACE WITH INCREASED HYDROPHILICITY

CROSS-REFERENCE TO RELATED APPLICATIONS

This application is a continuation of U.S. patent application Ser. No. 13/648,837, filed Oct. 10, 2012 (now U.S. Pat. No. 8,852,672) which is a continuation of U.S. patent application Ser. No. 12/359,780, filed Jan. 26, 2009 (now U.S. Pat. No. 8,309,162) which claims the benefit of U.S. Provisional Application No. 61/137,293, filed Jul. 28, 2008 and U.S. Provisional Application No. 61/062,577, filed Jan. 28, 2008, which are hereby incorporated by reference in their entireties.

FIELD OF THE INVENTION

This invention relates generally to implants and, in particular, to a dental implant having salt residuals deposited thereon and methods of making the same.

BACKGROUND OF THE INVENTION

It is becoming more common to replace a missing tooth with a prosthetic tooth that is placed upon and attached to a dental implant. Dental implants are often comprised of metal and metal alloys, including titanium (Ti) and titanium alloys. The dental implant serves as an artificial root that integrates with the bone tissue of the mouth below the gingiva.

For the dental implant to function successfully, sufficient osseointegration is required. In other words, a direct chemical bond between the implant and the bone must be formed and retained. Osseointegration materials may be incorporated onto the surface of the implant to help enhance the osseointegration process. Non-limiting examples of osseointegration materials include calcium phosphate ceramic materials such as hydroxyapatite, which is particularly chemically stable and osseoconductive.

To provide sufficient long-term behavior of an implant having an osseointegration compound on the surface, there must be a sufficient bond strength between the implant and the compound. Moreover, the compound is desirably sufficiently biostable such that the rate of dissolution of the compound is low.

The present invention is directed to an improved implant having salt residual deposits deposited on the implant surface for increasing the rate and extent of osseointegration and methods of forming the same.

SUMMARY OF THE INVENTION

The present invention relates to a method of increasing the hydrophilicity of an implant to be implanted into living bone. The method comprises the act of depositing non-toxic salt residuals on the surface of the implant by exposing the surface to a solution including the non-toxic salts. The method further comprises the act of drying the implant.

According to another process of the present invention, a method of forming an implant to be implanted into living bone comprises the act of roughening at least a portion of the implant surface to form a roughened surface. The method further comprises the act of increasing the hydrophilicity of the roughened surface by depositing non-toxic salt residuals on the roughened surface by exposing the roughened surface to a solution including the non-toxic salt.

According to another process of the present invention, a method of forming a dental implant made of titanium or titanium alloy comprises the act of removing a native oxide layer from a threaded bottom portion of the dental implant. The method further comprises the act of acid etching the threaded bottom portion to form a roughened surface having an array of micro scale irregularities having peak-to-valley heights not greater than about 20 microns. The method further comprises the act of depositing discrete hydroxyapatite nanocrystals on the roughened surface by exposure to a solution comprising 2-methoxyethanol solvent and the hydroxyapatite nanocrystals. The method further comprises the act of depositing salt residuals on the roughened surface by exposure to a solution comprising non-toxic salts. The salt residuals increase the hydrophilicity of the implant surface.

According to one embodiment of the present invention, a dental implant comprises a head portion having a non-rotational feature. The dental implant further comprises a lowermost end opposing the head portion. The dental implant further comprises a threaded bottom portion for engaging bone between the head portion and the lowermost end. The threaded bottom portion has a roughened surface with an array of microscale irregularities having peak-to-valley heights not greater than about 20 microns. The threaded bottom portion further includes discrete nanoparticles located on the roughened surface. The nanoparticles include hydroxyapatite nanocrystals. The threaded bottom portion further includes salt residuals deposited thereon.

According to another process of the present invention, a method of increasing the hydrophilicity of an implant to be implanted into living bone comprises the act of depositing non-toxic salt residuals on the surface of the implant by immersing at least a portion of the implant in a solution including sodium chloride, potassium chloride, calcium chloride, sodium lactate, or combinations thereof. The method further comprises the act of drying the implant. The contact angle formed by a deionized water droplet on the surface of the implant ranges from about 5° to about 65°.

According to another process of the present invention, a method of forming an implant to be implanted into living bone is disclosed. The method comprises the act of grit blasting at least a portion of the implant surface with a grit blast media. The method further comprises the act of removing residual grit blast media. The method further comprises the act of roughening the grit blasted portion of the implant surface to form a roughened surface. The method further comprises the act of depositing discrete hydroxyapatite nanocrystals on the roughened surface. The method further comprises the act of optionally increasing the hydrophilicity of the roughened surface by depositing non-toxic salt residuals on the roughened surface by exposing the roughened surface to a solution including the non-toxic salt.

The above summary of the present invention is not intended to represent each embodiment, or every aspect, of the present invention. This is the purpose of the figures and the detailed description which follow.

BRIEF DESCRIPTION OF THE DRAWINGS

The foregoing and other advantages of the invention will become apparent upon reading the following detailed description and upon reference to the drawings.

DETAILED DESCRIPTION

The present invention is directed to implants having salt residuals deposited thereon and methods of making the same. The salt residuals have been shown to increase the hydrophilicity (i.e., wettability) of the implant surface, thereby assisting in increasing the rate and extent of osseointegration with bone. An implant in the context of the present invention means a device intended to be placed within a human body such as to connect skeletal structures (e.g., a hip implant) or to serve as a fixture for a body part (e.g., a fixture for an artificial tooth). Although the remainder of this application is directed to a dental implant, it is contemplated that the present invention may also be applied to other (e.g., medical) implants.

Figure 1:
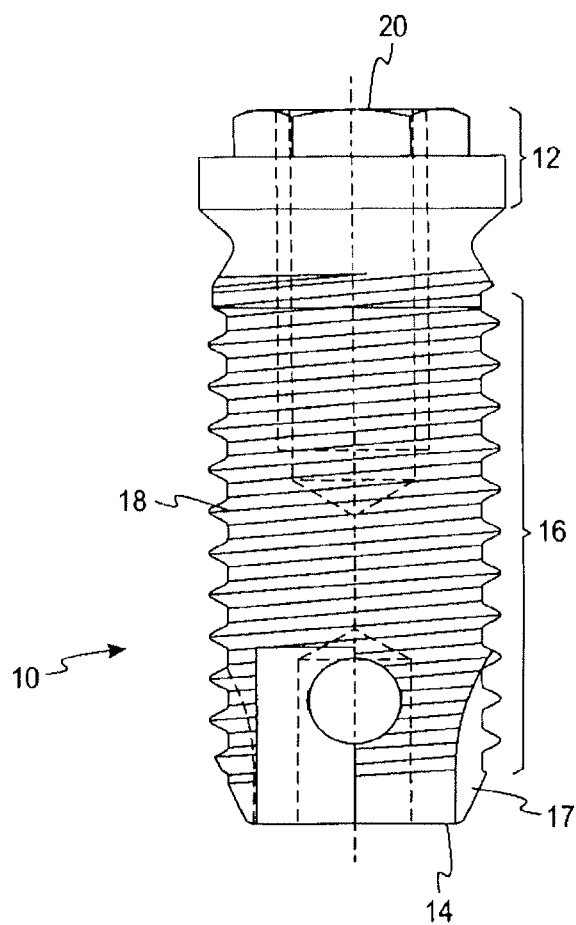
FIG. 1 is a side view of an implant according to one embodiment.

FIG. 1 shows a standard dental implant 10 that includes an head portion 12, a lowermost end 14, and a threaded bottom portion 16. The implant 10 may, for example, be made of titanium, tantalum, cobalt, chromium, stainless steel, or alloys thereof. It is contemplated that other materials such as ceramics or ceramic-titanium combinations may also be used. FIGS. 2a-c, 3a-c, and 4a-b, which are discussed below, describe alternative implant designs that may also be used with the present invention.

In the implant 10 of FIG. 1, the head portion 12 includes a non-rotational feature. In the embodiment shown, the non-rotational feature includes a polygonal boss 20 that may be engageable with a tool that screws the implant 10 into bone tissue. In the illustrated embodiment, the polygonal boss 20 is hexagonal. The polygonal boss 20 may also be used for non-rotationally engaging a correspondingly shaped socket on a restorative or prosthetic component that is attached to the implant 10.

The exterior of the threaded bottom portion 16 facilitates bonding with bone or gingiva. The threaded bottom section 16 includes a thread 18 that makes a plurality of turns around the implant 10. The threaded bottom portion 16 may further include a self-tapping region with incremental cutting edges 17 that allows the implant 10 to be installed without the need for a bone tap. Examples of incremental cutting edges 17 are described in detail in U.S. Pat. No. 5,727,943, entitled "Self-Tapping, Screw-Type Dental Implant," which is incorporated by reference in its entirety.

Figure 2B:
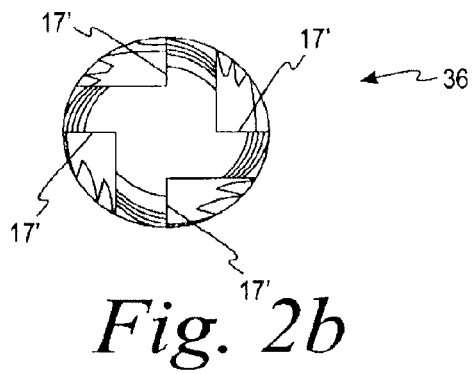
FIGS. 2a, 2b, and 2c, are a side view, an insertion end view, and a gingival end view, respectively, of an implant according to a second embodiment.
Figure 2A:
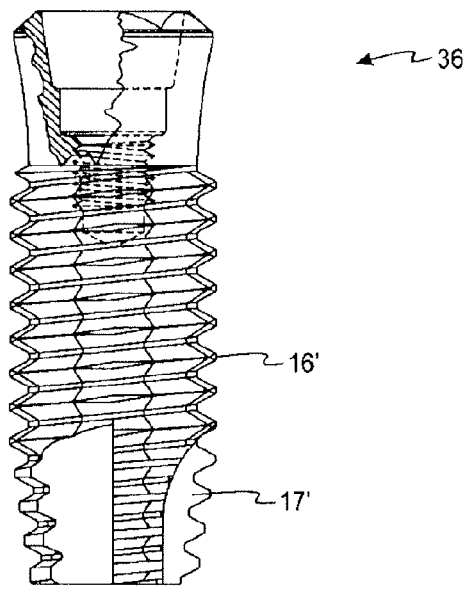
Figure 2C:
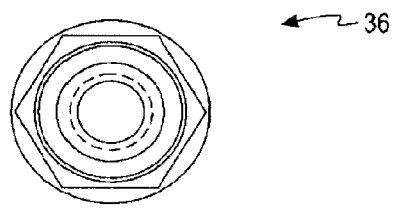

FIGS. 2a-c disclose an implant 36 that differs from the implant 10 of FIG. 1 in the details of the cutting edges 17' and the contours of the threads defining the exterior of the threaded bottom portion 16'. When viewed in the cross-section (see FIG. 1b), the threaded outer surface 16' is non-circular in the region of the threads and/or the troughs between the threads. This type of thread structure is described in detail in U.S. Pat. No. 5,902,109, entitled "Reduced Friction, Screw-Type Dental Implant," which is incorporated by reference in its entirety. One or more non-rotational features may also be present on the interior bore of the implant.

Figure 3B:
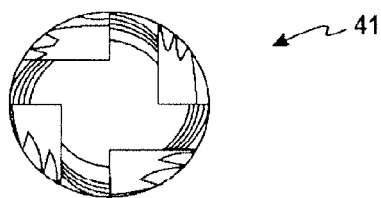
FIGS. 3a, 3b, and 3c, are a side view, an insertion end view, and a gingival end view, respectively, of an implant according to a third embodiment.
Figure 3A:
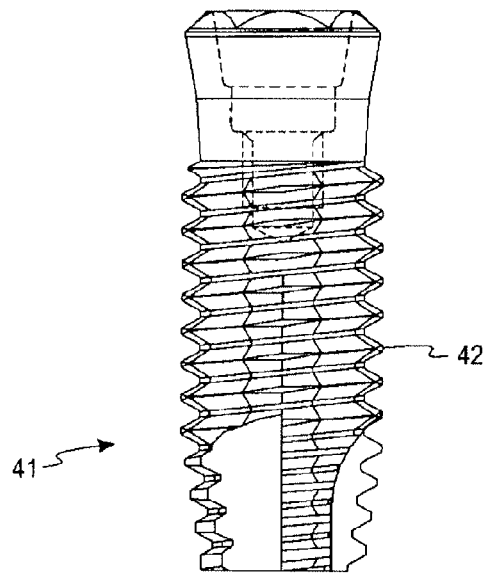
Figure 3C:
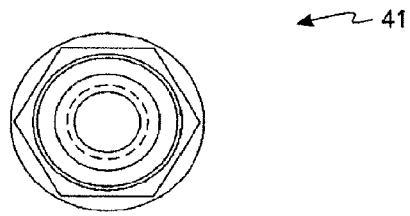

In FIGS. 3a-c, an implant 41 having a wide diameter in the region of the threaded bottom portion 42 is illustrated. The diameter is in the range of from about 4.5 mm to about 6.0 mm with the diameter of 5.0 mm being a fairly common dimension for a wide diameter implant. Such an implant 41 is useful to engage one or both cortical bones to provide enhanced stability, especially during the period of time after installation.

Figure 4B:
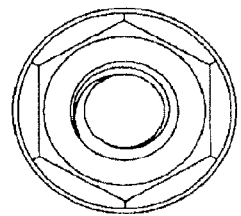
FIGS. 4a and 4b are a side view, an end view, and a cross-sectional view, respectively, of an implant according to a fourth embodiment.
Figure 4A:
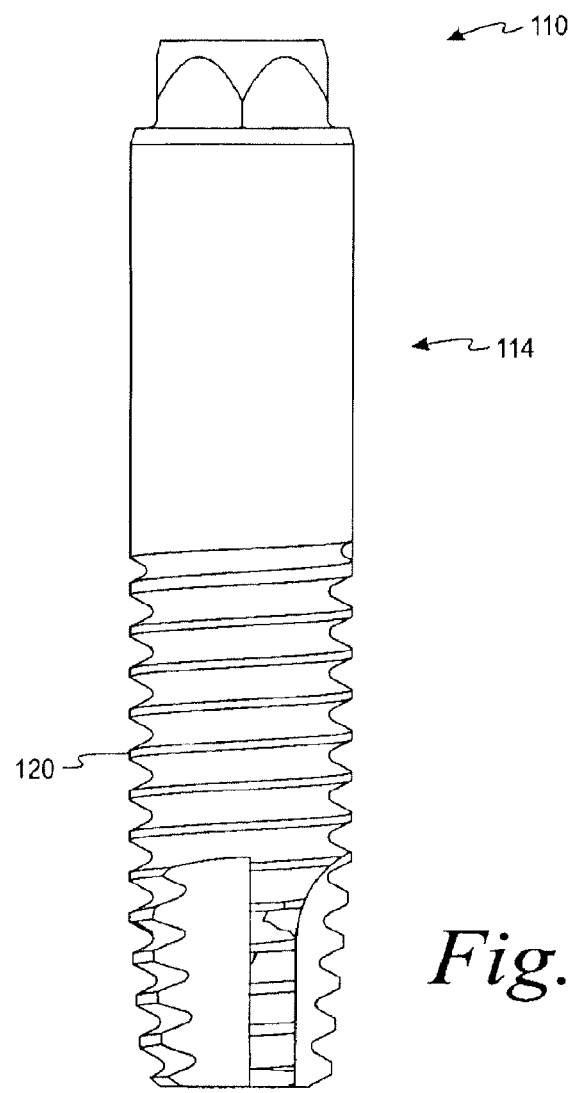

FIGS. 4a-b illustrate an implant 110 according to another embodiment that may be used with the present invention. The implant 110 includes an elongated middle section 114 designed to extend through the gingiva. Preferably, it is a smooth surface that includes a titanium nitride coating so the underlying titanium or titanium alloy is not readily seen through the gingiva. The implant 110 also includes a threaded portion 120 that may include various thread structures and is preferably roughened to increase the osseointegration process. It is contemplated that implants other than those illustrated in FIGS. 1-4 may be used with the present invention.

Figure 5:
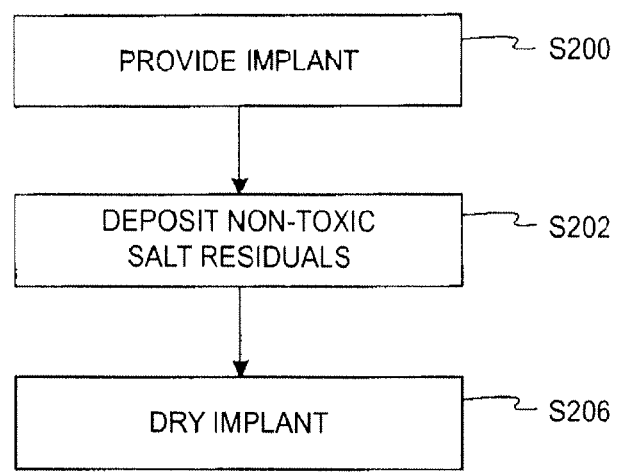
FIGS. 5-6 are flow diagrams detailing methods of forming an implant according to embodiments of the present invention.

According to the present invention, a controlled deposition of salt residuals overlies at least a portion (e.g., the threaded bottom portion) of the surface of an implant. Referring now to FIG. 5, a general method of forming an implant according to one embodiment of the present invention is illustrated. An implant comprised of titanium, a titanium alloy (e.g., titanium 6AL-4V ELI alloy), stainless steel, ceramic, or the like is provided at step s200. In this embodiment, the implant is machined, and its final surface configuration is generally smooth. At step s202, the implant is immersed in a solution including a specific chemistry of non-toxic salts. The implant is then dried at step s206. Following the process of FIG. 5, the treated implant includes a controlled salt residual on its surface, which generally increases the hydrophilicity of the implant surface. The increased hydrophilicity should increase the rate and extent of osseointegration.

Figure 6:
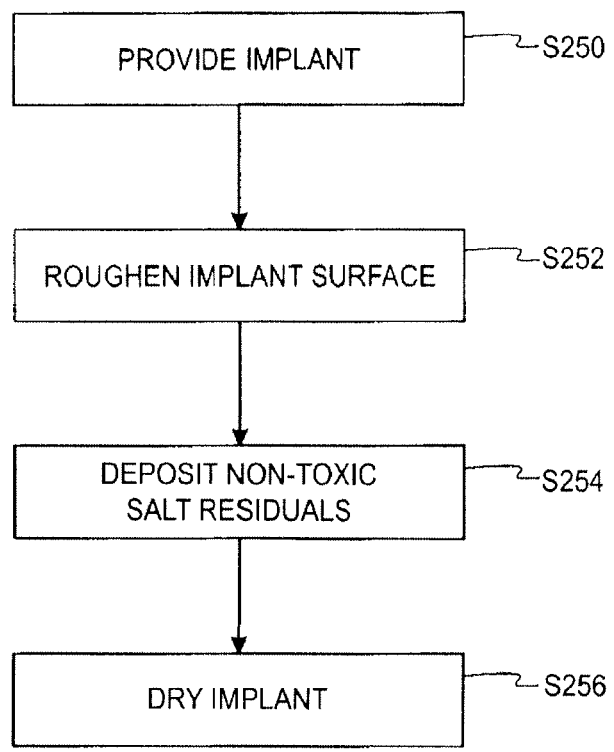
Figure 7:
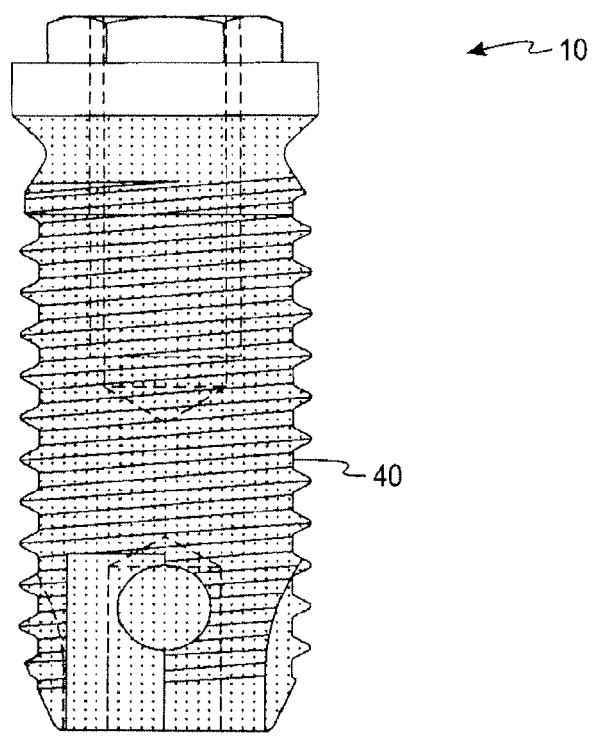
FIG. 7 is a side view of the implant of FIG. 1 with a roughened outer surface.

Turning now to FIG. 6, another general method of depositing salt residuals onto the surface of an implant is set forth according to another embodiment of the present invention. At step s250, an implant is provided. At least a portion of the implant surface is roughened at step s252. As an example, FIG. 7 shows the implant 10 of FIG. 1 having a roughened surface 40. Salt residuals are then deposited onto the roughened surface of the implant at step s254. The implant may then be dried at step s256.

Figure 8A:
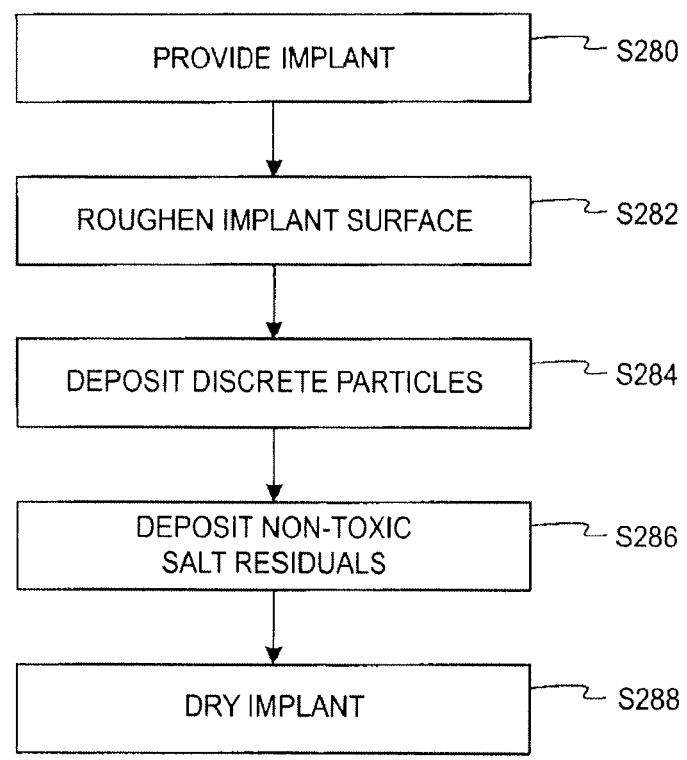
FIGS. 8a-c are flow diagrams detailing methods of forming an implant according to other embodiments of the present invention.

Referring to FIG. 8a, another method of forming an implant is shown. At step s280, an implant is provided. At least a portion of the implant surface is roughened at step s282. Discrete particles (e.g., nanoparticles) comprising a material promoting osseointegration are then deposited on the roughened surface of the implant at step s284. Salt residuals are then deposited onto the roughened surface of the implant at step s286. The implant is then dried at step s288

Figure 8B:
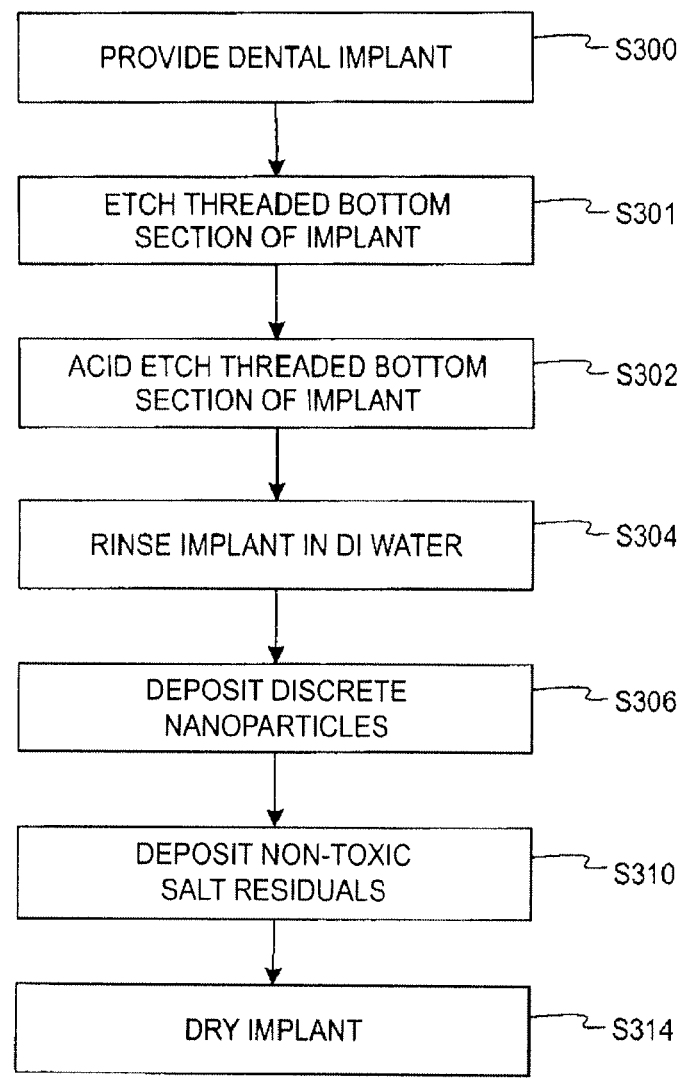

Referring to FIG. 8b, a more detailed method of depositing salt residuals onto the surface of a dental implant is illustrated according to another embodiment of the present invention. A threaded dental implant comprised of titanium, a titanium alloy (e.g., titanium 6AL-4V ELI alloy), stainless steel, or the like is provided at step s300. The surface of the dental implant is generally clean and dry. A threaded bottom portion of the implant is etched to remove a native oxide layer from the implant surface at step s301. The native oxide layer may be removed by a first acid solution, which may include aqueous hydrofluoric acid. The threaded bottom portion is then acid etched a second time to form a roughened surface at step s302. The acid etching step may include a mixture of sulfuric and hydrochloric acids. The roughened surface forms a substantially uniform array of microscale irregularities for enhancing the integration of the implant with bone or other biological interfaces. "Microscale," as used herein, should be understood to describe an article or feature generally measured in microns such as, for example, 1 micron to 100 microns. The irregularities may include microscale cone-shaped elements and generally have peak-to-valley heights not greater than about 20 microns and are preferably about 1 micron to about 10 microns. This type of roughening method utilized on commercially pure (CP) titanium is described in detail in U.S. Pat. No. 5,876,453 entitled "Implant Surface Preparation," which is incorporated by reference in its entirety. An additional roughening method utilized on Titanium 6AL-4V ELI alloy is described in detail in U.S. Pat. App. Pub. No. 2004/0265780 entitled "Surface Treatment Process for Implants Made of Titanium Alloy," which is also incorporated by reference in its entirety. It is contemplated that other surface roughening techniques including, but not limited to, grit blasting and titanium plasma spray may be used. After these acid-etching steps, the implant may then be rinsed in hot deionized water (e.g., 70° C. to 100° C.) to remove any acid residuals and to potentially enhance titanium hydroxide groups on the surface at step s304.

Discrete nanoparticles comprising a material promoting osseointegration are then deposited on the roughened surface of the implant at step s306. In one embodiment, the nanoparticles include hydroxyapatite (HA) nanocrystals. The HA nanocrystals may be on the order of about 20 nanometers to about 100 nanometers. The discrete HA nanocrystals may be deposited onto the roughened surface by exposing the implant to a solution comprising 2-methoxyethanol solvent and HA nanocrystals. This type of deposition process is described in U.S. Pat. App. Pub. Nos. 2007/0110890 and 2007/0112353, which have been incorporated by reference herein in their entireties.

Salt residuals are then deposited onto the surface of the implant at step s310. The salt residuals may include, but are not limited to, sodium chloride, potassium chloride, calcium chloride, and sodium lactate. The salt residuals may be introduced onto the surface of the implant by dipping or immersing the implant in a non-toxic salt solution. The non-toxic salt solution may, for example, be physiological saline solution or lactated Ringer's solution. The implant is then dried at step s314. The drying process may be conducted at ambient temperatures or at elevated temperatures. Additional acts may then be performed including, but not limited to, sterilization (e.g., gamma sterilization) and packaging.

According to another method of the present invention, salt residuals are deposited onto an implant surface having nanoparticles of a material promoting osseointegration (e.g., HA nanocrystals) deposited thereon, where the nanoparticles were deposited on the implant surface without first roughening the surface of the implant.

Figure 8C:
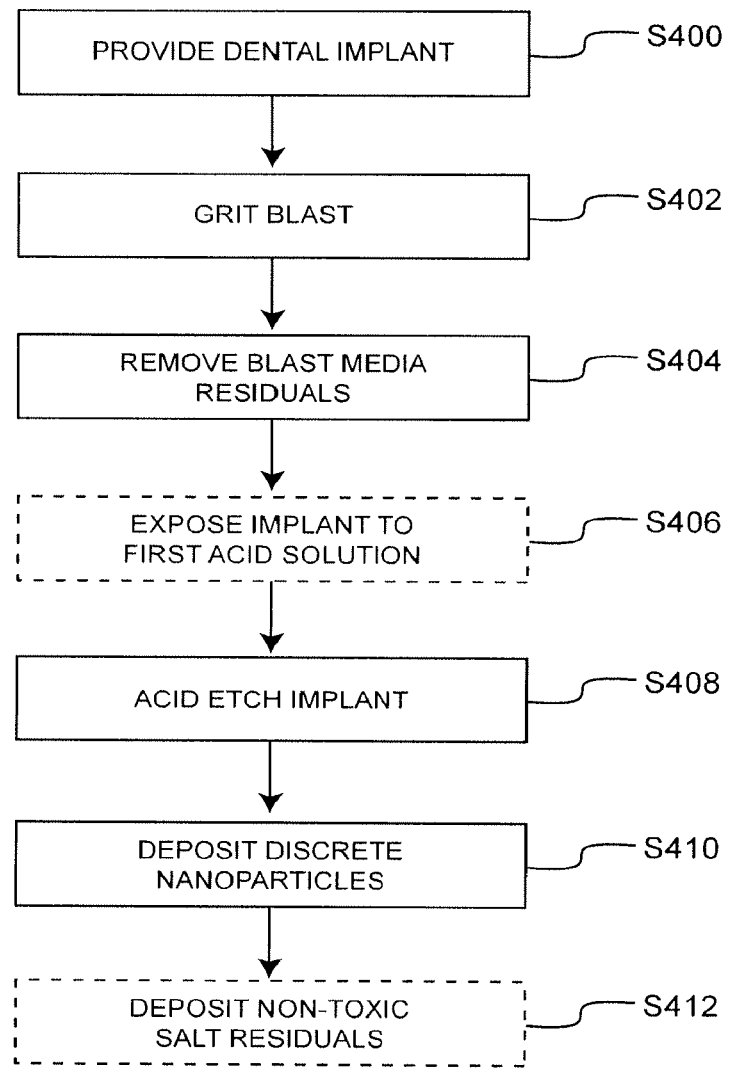

Referring to FIG. 8c, a method of forming a dental implant is illustrated according to another embodiment of the present invention. A dental implant comprised of titanium, a titanium alloy (e.g., titanium 6AL-4V ELI alloy), stainless steel, or the like is provided at step s400. At least a portion of the implant surface is then grit blasted to remove surface oxides and/or contamination at step s402. Blast media used in step s402 may include a resorbable blast media including, but not limited to, calcium phosphate. The overall surface topography of the resulting grit blasted implant surface generally includes peak-to-valley heights of about 10 microns or less. The grit blasting step s402 also assists in removing a native oxide layer from the implant surface.

Blast media residuals are then removed from the implant surface at step s404. The blast media residuals may be removed by, for example, exposing the implant to an acid (e.g., nitric acid) or acid solution.

At optional step s406, the implant surface is exposed to a first acid solution, which may include hydrofluoric acid, to prepare the implant for micron-scale etching (i.e., step s408). The first acid solution assists in cleaning the grit blasted implant surface and smoothening irregularities (e.g., from the implant machining process) thereon. The first acid solution also assists in removing any native oxide that may have reformed on the implant surface. It has been found that step s406 may be desirable for implants made of commercially pure (CP) titanium and may be eliminated for implants made of titanium alloy (e.g., titanium 6AL-4V ELI).

At step s408, The implant surface is then acid etched in a second acid solution to form a roughened surface including a substantially uniform array of microscale irregularities for enhancing the integration of the implant with bone or other biological interfaces. The acid etching step s408 imparts a separate micron level topography including average peak-to-peak distances of about 1 micron to about 3 microns. As described above with respect to step s302 of FIG. 8b, the acid etching step s408 may include a mixture of sulfuric and hydrochloric acids.

As described above with respect to step s306 of FIG. 8b, discrete nanoparticles comprising a material promoting osseointegration (e.g., hydroxyapatite) may then be deposited on the roughened implant surface at step s410. The nanoparticles generally range in size from about 1 nanometer to about 100 nanometers and are applied over about 25% to about 75% of the implant surface, without an intermediate layer. As described above with respect to step s310 of FIG. 8b, saline salt residuals (e.g., sodium lactate) may then be deposited, as a thin layer or as discrete residuals, onto the implant surface at optional step s412.

The implant surface may be characterized utilizing Field Emission Scanning Electron microscopy (FESEM). Depending upon the resolution of the instrument, the surface of the implant may typically be witnessed at magnifications of 10kX of greater. In the examples provided below, the SEM model was the JSM 6460LV (JEOL USA Inc., Peabody, Mass.), and the images were taken at 10kX magnification.

The changes in the surface chemistry of the implants may be analyzed by electron dispersion spectroscopy (EDS). In the examples below, an Oxford Instruments EDS (Oxfordshire, United Kingdom) was used. Additionally, the data provided in the tables of the examples below was obtained by analyzing and averaging two 100×200 micron spots of the respective titanium 6AL-4V ELI alloy disks.

The effect of the salt residuals on the hydrophilicty of the implants may be verified by measuring contact angles. The contact angle is a quantitative measure of the spread of a droplet on the surface, and is subsequently a measurement of its hydrophilicity. A smaller contact angle represents a more hydrophilic surface. In the examples below, a deionized water drop was injected onto the disk surfaces. The reaction of the droplet with the surface was recorded via imaging. During review of the imaging, the contact angle of the water on the disk surface was measured. The instrument used to measure the contact angles was an MD-OCA contact angle meter (Future Scientific, New York, N.Y.) using SCA20 software (DataPhysics, Germany).

Example 1

Fifteen titanium 6AL-4V ELI alloy disks were machined using typical turning techniques. After machining, the disks were cleaned with an aqueous detergent including ultraonics to remove residual machining fluid. The disks were then rinsed thoroughly with deionized water and oven dried.

The fifteen titanium 6AL-4V ELI alloy disks were then separated into three groups. Group 1 included five disks and was utilized as a control group. Group 2 included five disks that were immersed in physiological saline solution (about 0.9 w/w % NaCl). After being soaked in the physiological saline solution for about five minutes, the disks were oven dried utilizing a forced convection oven at a temperature of about 100° C. Group 3 included five disks that were immersed in lactated Ringer's solution (about 0.6 w/w % NaCl, about 0.3 w/w % $C_5H_5NaO_3$, about 0.03 w/w % KCl, and about 0.02 w/w % $CaCl_2$). After being soaked in the lactated Ringer's solution for about five minutes, the disks were oven dried utilizing a forced convection oven at 100° C. The disks were then packaged in polyethylene zip-lock type bags.

One disk from each of the three groups was then analyzed using EDS to determine changes in the surface chemistry. The results are summarized in Table 1 below.

TABLE 1

|  | Group 1 - Control (w/w %), n = 2 | Group 2 - Physiological Saline (w/w %), n = 2 | Group 3 - Lactated Ringer's (w/w %), n = 2 |
| --- | --- | --- | --- |
| Titanium | 87.87 | 79.85 | 43.58 |
| Vanadium | 3.84 | 2.1 | 0 |
| Aluminum | 6.28 | 5.4 | 3.06 |
| Oxygen | 0 | 0 | 14.86 |
| Carbon | 2.01 | 1.04 | 11.79 |
| Calcium | 0 | 0 | 0 |
| Phosphorous | 0 | 0 | 0 |
| Sodium | 0 | 5.67 | 12.94 |
| Chloride | 0 | 5.95 | 13.48 |
| Potassium | 0 | 0 | 0.305 |
| Total | 100 | 100 | 100 |

As shown in Table 1, the surface of the disk of the control group (Group 1) did not include any salt residuals, while the surfaces of the disks of Groups 2 and 3 included salt residuals. More specifically, the surface of the disk that was immersed in physiological saline solution (Group 2) included 5.67 w/w % sodium and 5.95 w/w % chloride (total: 11.62 w/w % salts). The surface of the disk that was immersed in lactated Ringer's solution (Group 3) included 14.86 w/w % oxygen, 11.79 w/w % carbon, 12.94 w/w % sodium, 13.48 w/w % chloride, and 0.305 w/w % potassium (total: 53.375 w/w %).

Figure 9A:
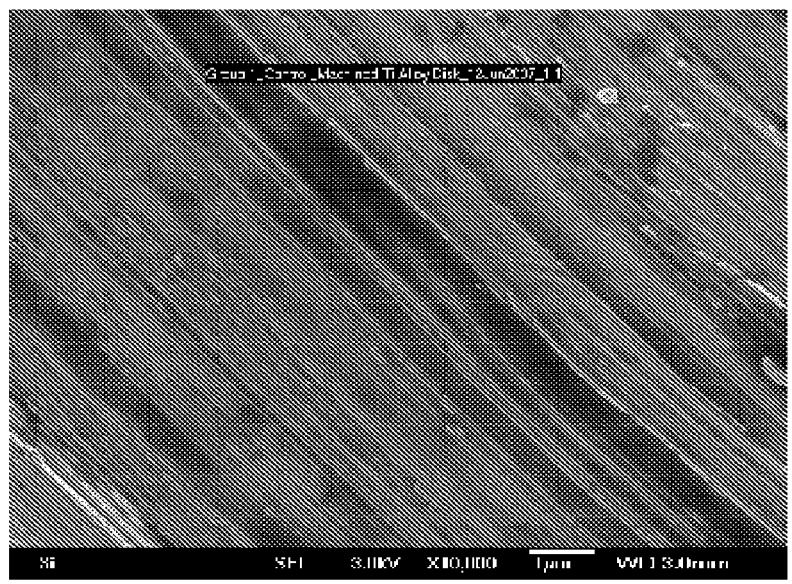
FIG. 9a is a field emission scanning electron microscope (FESEM) image showing a machined titanium alloy disk at 10kX.
Figure 9B:
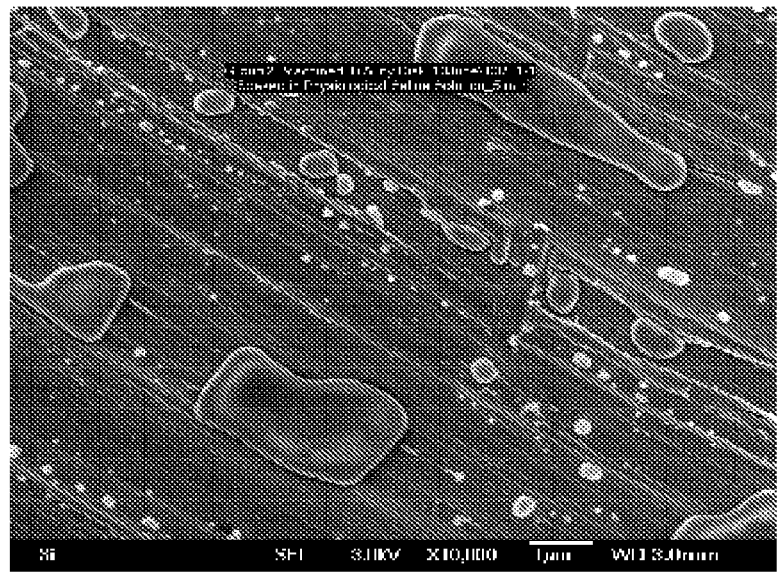
FIG. 9b is an FESEM image showing a machined titanium alloy disk at 10kX after being soaked in physiological saline solution.
Figure 9C:
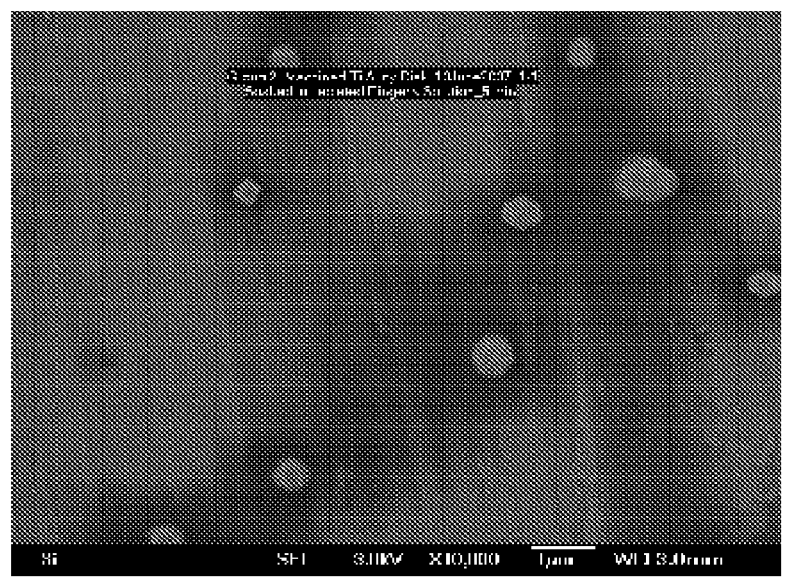
FIG. 9c is an FESEM image showing a machined titanium alloy disk at 10kX after being soaked in lactated Ringer's solution.

The same disks were then imaged using an FESEM to show the variations in the surface chemistry of the various disks. FIG. 9a shows the disk from the control group (Group 1), FIG. 9b shows the disk that was immersed in physiological saline solution (Group 2), and FIG. 9c shows the disk that was immersed in lactated Ringer's solution (Group 3).

Contact angles were then measured on each side of four disks from each group. The results are included in Table 2 below.

TABLE 2

| Sample | Group 1 - Control (degrees) | Group 2 - Physiological Saline (degrees) | Group 3 - Lactated Ringer's (degrees) |
| --- | --- | --- | --- |
| 1 | 86 | 68 | 18 |
| 2 | 80 | 57 | 32 |
| 3 | 76 | 76 | 21 |
| 4 | 87 | 77 | 30 |
| 5 | 85 | 73 | 31 |
| 6 | 82 | 79 | 31 |

TABLE 2-continued

| Sample | Group 1 - Control (degrees) | Group 2 - Physiological Saline (degrees) | Group 3 - Lactated Ringer's (degrees) |
|---|---|---|---|
| 7 | 81 | 70 | 49 |
| 8 | 78 | 59 | 28 |
| Mean | 81.9 | 69.9 | 30.0 |
| SD | 3.9 | 8.2 | 9.2 |

As shown in Table 2, the disks having salts deposited thereon—those of Groups 2 and 3—had the lowest contact angles (69.9° and 30.0°, respectively) and thus, were the most hydrophilic. Furthermore, the disks of Group 3, which were immersed in lactated Ringer's solution, were determined to be considerably more hydrophilic than the disks of Group 2, which were immersed in physiological saline solution. The disks of the control group, Group 1, which did not have any salt residuals deposited thereon, had the highest contact angles and, thus, were the least hydrophilic.

Example 2

Fifteen titanium 6AL-4V ELI alloy disks were machined using typical turning techniques. After machining, the disks were cleaned with an aqueous detergent including ultraonics to remove residual machining fluid. The disks were then rinsed thoroughly with deionized water and oven dried. After oven drying, the disks were roughened using a dual acid etching process, described in U.S. Pat. App. Pub. No. 2004/0265780, which has been incorporated by reference herein, to produce an Osseotite® surface. The roughening process resulted in irregularities having peak-to-valley heights of no more than 10 microns. The disks were then oven dried.

The fifteen Osseotite® titanium 6AL-4V ELI alloy disks were then separated into three groups. Group 1 included five disks and was utilized as a control group. Group 2 included five disks that were immersed in physiological saline solution for about five minutes and then oven dried utilizing a forced convection oven at a temperature of 100° C. Group 3 included five disks that were immersed in lactated Ringer's solution for about five minutes and then oven dried utilizing a forced convection oven at 100° C. The disks were then packaged in polyethylene zip-lock type bags.

One disk from each of the three groups was then analyzed using EDS to determine changes in the surface chemistry. The results are summarized in Table 3 below.

TABLE 3

| | Group 1 - Control (w/w %), n = 2 | Group 2 - Physiological Saline (w/w %), n = 2 | Group 3 - Lactated Ringer's (w/w %), n = 2 |
|---|---|---|---|
| Titanium | 88.83 | 61.2 | 53.42 |
| Vanadium | 4.58 | 4.53 | 2.51 |
| Aluminum | 5.87 | 4.48 | 3.77 |
| Oxygen | 0 | 0 | 10.86 |
| Carbon | 0.73 | 3.91 | 8.1 |
| Calcium | 0 | 0 | 0 |
| Phosphorous | 0 | 0 | 0 |
| Sodium | 0 | 11.87 | 10.36 |
| Chloride | 0 | 14.02 | 10.99 |
| Potassium | 0 | 0 | 0 |
| Total | 100 | 100 | 100 |

As shown in Table 3, the surface of the disk of the control group, Group 1, did not include any salt residuals, while the surfaces of the disks of Groups 2 and 3 did include salt residuals. More specifically, the surface of the disk that was immersed in physiological saline solution (Group 2) included 11.87 w/w % sodium, and 14.02 w/w % chloride (total: 25.89 w/w % salts). The surface of the disk that was immersed in lactated Ringer's solution (Group 3) included 10.86 w/w % oxygen, 8.1 w/w % carbon, 10.36 w/w % sodium and 10.99 w/w % chloride (total: 40.31 w/w %).

Figure 10A:
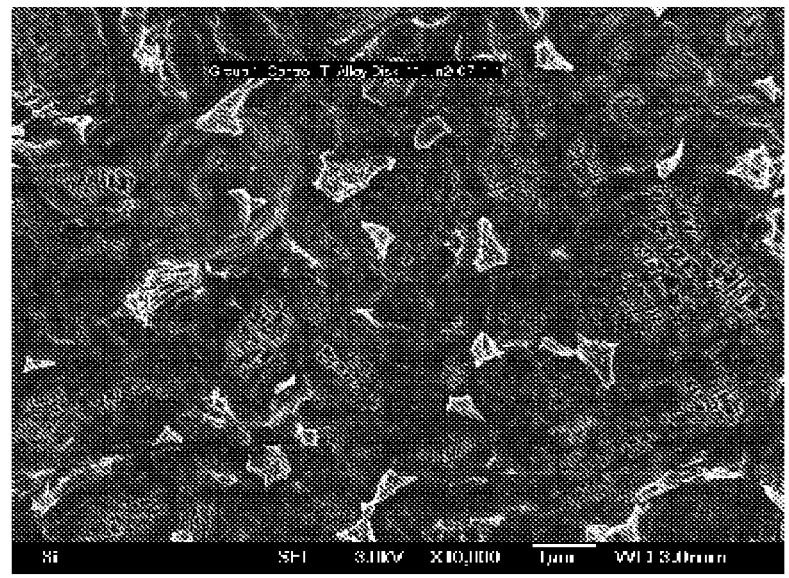
FIG. 10a is an FESEM image showing a dual acid etched titanium alloy disk at 10kX.
Figure 10B:
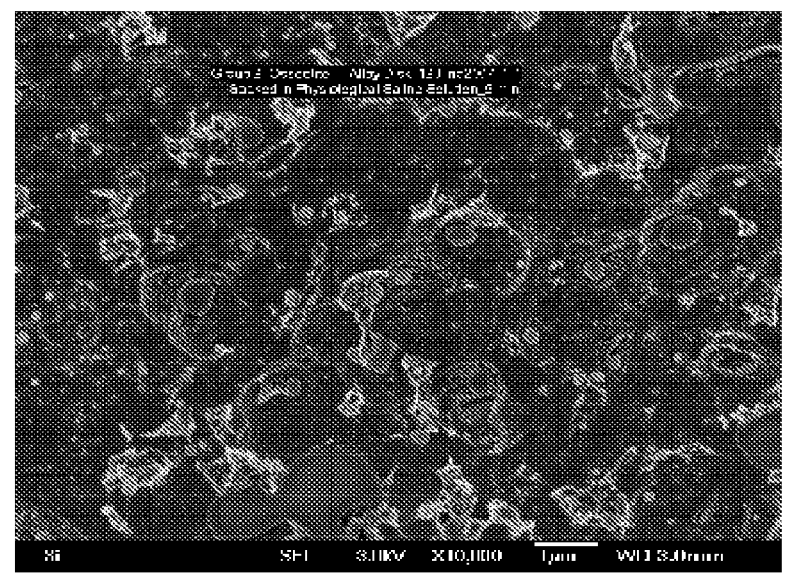
FIG. 10b is an FESEM image showing a dual acid etched titanium alloy disk at 10kX after being soaked in physiological saline solution.
Figure 10C:
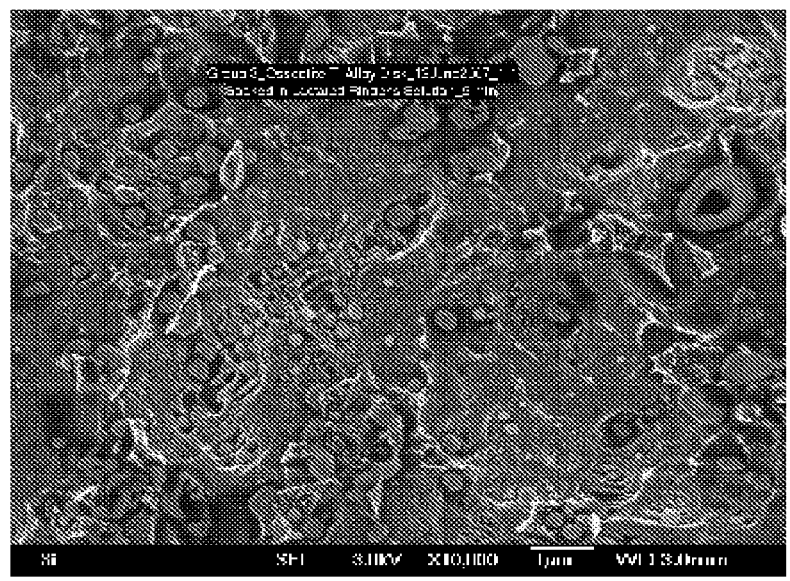
FIG. 10c is an FESEM image showing a dual acid etched titanium alloy disk at 10kX after being soaked in lactated Ringer's solution.

The same disks analyzed in Table 3 were then imaged using an FESEM to show the variations in the surface chemistry of the various disks. FIG. 10a shows the disk from the control group (Group 1), FIG. 10b shows the disk that was immersed in physiological saline solution (Group 2), and FIG. 10c shows the disk that was immersed in lactated Ringer's solution (Group 3).

Contact angles were then measured on each side of four disks from each group. The results are included in Table 4 below.

TABLE 4

| Sample | Group 1 - Control (degrees) | Group 2 - Physiological Saline (degrees) | Group 3 - Lactated Ringer's (degrees) |
|---|---|---|---|
| 1 | 90 | 58 | 10 |
| 2 | 93 | 60 | 9 |
| 3 | 94 | 65 | 12 |
| 4 | 96 | 53 | 11 |
| 5 | 86 | 56 | 7 |
| 6 | 85 | 60 | 8 |
| 7 | 82 | 59 | 8 |
| 8 | 82 | 61 | 12 |
| Mean | 88.5 | 59.0 | 9.6 |
| SD | 5.5 | 3.5 | 1.9 |

The results of Table 4 were consistent with the data of Table 2 of Example 1 above. Specifically, the disks having salts deposited thereon—those of Groups 2 and 3—had the lowest contact angles and, thus, were the most hydrophilic. Furthermore, the disks of Group 3, which were immersed in lactated Ringer's solution, were determined to be considerably more hydrophilic than the disks of Group 2, which were immersed in physiological saline solution. The disks of the control group, Group 1, which did not have any salt residuals deposited thereon, had the highest contact angles and, thus, were the least hydrophilic.

Furthermore, comparing the contact angle measurements of Table 4 to those in Table 2 of Example 1 above shows that the contact angles of the disks that were roughened prior to immersion in the salt solution (i.e., those of Example 2) had generally lower contact angles and were, thus, more hydrophilic than the disks that were not roughened (i.e., those of Example 1).

Example 3

Fifteen titanium 6AL-4V ELI alloy disks were machined using typical turning techniques. After machining, the disks were cleaned with an aqueous detergent including ultraonics to remove residual machining fluid. The disks were then rinsed thoroughly with deionized water and oven dried. After oven drying, the disks were roughened using the dual acid-etched process described in U.S. Pat. App. Pub. No. 2004/0265780, which has been incorporated by reference herein. Discrete crystals of hydroxyapatite were then deposited on the roughened surfaces of the disks using the process described in U.S. Pat. App. Pub. Nos. 2007/0110890 and 2007/0112353, which have been incorporated by reference herein, to produce a Biomet 3i NanoTite™ surface. The disks were then oven dried.

The fifteen Biomet 3i NanoTite™ titanium 6AL-4V ELI alloy disks were then separated into three groups. Group 1 included five disks and was utilized as a control group. Group 2 included five disks that were immersed in physiological saline solution for about five minutes and then oven dried utilizing a forced convection oven at a temperature of 100° C. Group 3 included five disks that were immersed in lactated Ringer's solution for about five minutes and then oven dried utilizing a forced convection oven at 100° C. The disks were then packaged in polyethylene zip-lock type bags.

One disk from each of the three groups was then analyzed using EDS to determine changes in the surface chemistry. The results are summarized in Table 5 below.

TABLE 5

|  | Group 1 - Control (w/w %) | Group 2 - Physiological Saline (w/w %) | Group 3 - Lactated Ringer's (w/w %) |
| --- | --- | --- | --- |
| Titanium | 82.86 | 74.55 | 62.18 |
| Vanadium | 1.64 | 4.06 | 3.52 |
| Aluminum | 5.28 | 5.03 | 4.13 |
| Oxygen | 6.9 | 5.10 | 15.67 |
| Carbon | 1.45 | 1.71 | 5.80 |
| Calcium | 1.22 | 0.71 | 1.08 |
| Phosphorous | 0.67 | 0.31 | 0.15 |
| Sodium | 0 | 4.24 | 4.17 |
| Chloride | 0 | 4.32 | 2.90 |
| Potassium | 0 | 0 | 0.41 |
| Total | 100 | 100 | 100 |

As shown in Table 5, the surface of the disk of the control group (Group 1) did not include any salt residuals (except calcium and phosphate, which resulted from the deposition of discrete hydroxyapatite crystals), while the surfaces of the disks of Groups 2 and 3 included salt residuals. More specifically, the surface of the disk that was immersed in physiological saline solution (Group 2) included 4.24 w/w % sodium and 4.32 w/w % chloride (total: 8.56 w/w % sodium and chloride salts) that were not included in the control group (Group 1). The surface of the disk that was immersed in lactated Ringer's solution (Group 3) included 4.17 w/w % sodium, 2.90 w/w % chloride, and 0.41 w/w % potassium (total: 7.48 w/w % sodium, chloride, and potassium salts) that were not included in the control group (Group 1). Group 3 also included 15.67 w/w % oxygen and 5.80 w/w % carbon, which are directly related to the lactate salt ($NaC_3H_5O_3$).

Figure 11A:
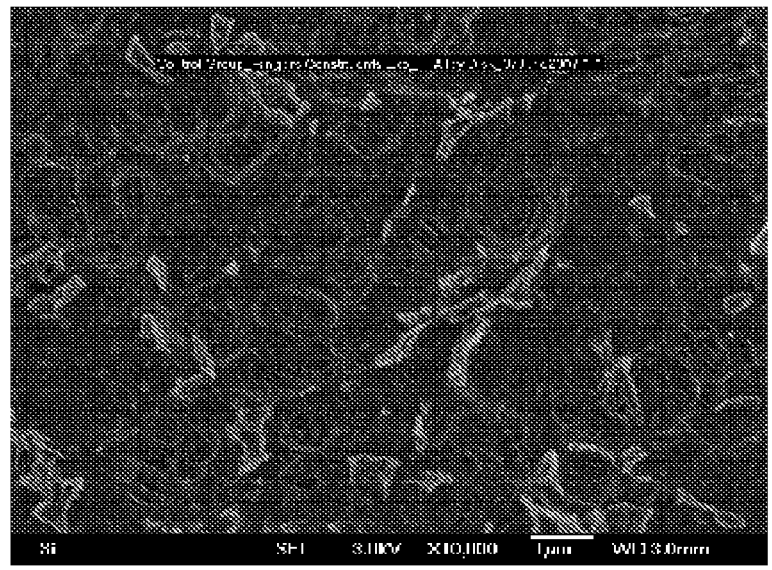
FIG. 11a is an FESEM image showing a dual acid etched titanium alloy disk having hydroxyapatite particles deposited thereon at 10kX.
Figure 11B:
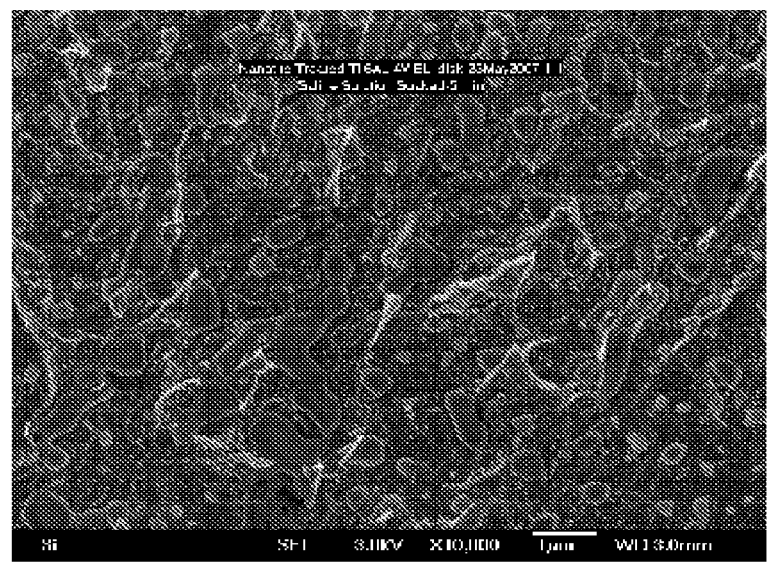
FIG. 11b is an FESEM image showing a dual acid etched titanium alloy disk having hydroxyapatite particles deposited thereon at 10kX after being soaked in physiological saline solution.
Figure 11C:
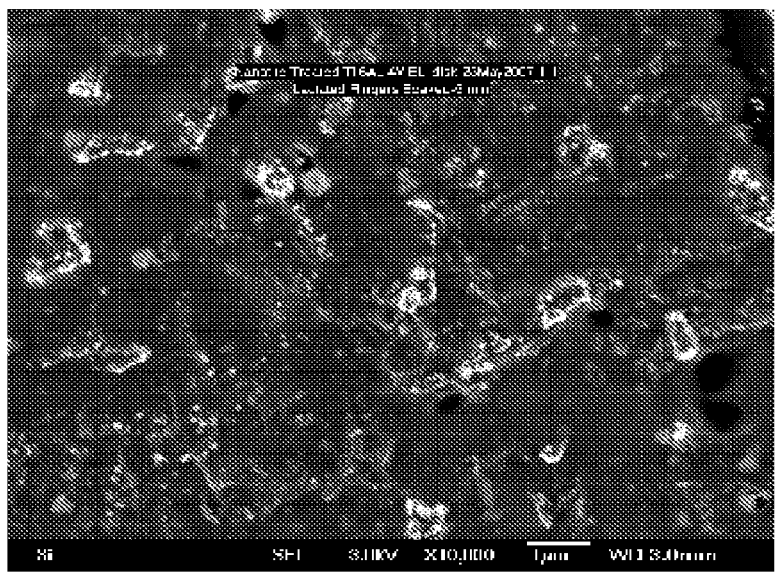
FIG. 11c is an FESEM image showing a dual acid etched titanium alloy disk having hydroxyapatite particles deposited thereon at 10kX after being soaked in lactated Ringer's solution.

The same disks were then imaged using an FESEM to show the variations in the surface chemistry of the various disks. FIG. 11a shows the disk from the control group (Group 1), FIG. 11b shows the disk that was immersed in physiological saline solution (Group 2), and FIG. 11c shows the disk that was immersed in lactated Ringer's solution (Group 3).

Contact angles were then measured on each side of four disks from each group. The results of this testing are included in Table 6 below.

TABLE 6

| Sample | Group 1 - Control (degrees) | Group 2 - Physiological Saline (degrees) | Group 3 - Lactated Ringer's (degrees) |
| --- | --- | --- | --- |
| 1 | 78 | 50 | 10 |
| 2 | 81 | 63 | 7 |
| 3 | 74 | 68 | 15 |
| 4 | 76 | 65 | 13 |
| 5 | 85 | 66 | 5 |
| 6 | 91 | 55 | 5 |
| 7 | 80 | 59 | 8 |
| 8 | 78 | 60 | 5 |
| Mean | 80.4 | 60.8 | 8.5 |
| SD | 5.4 | 6.0 | 3.9 |

The results of Table 6 were consistent with the data of Tables 2 and 4 of Example 1 and 2, respectively, above. Specifically, the disks having salts deposited thereon—those of Groups 2 and 3—had the lowest contact angles and, thus, were the most hydrophilic. Furthermore, consistent with the data of Table 4 above, the disks that were immersed in lactated Ringer's solution (Group 3) were determined to be considerably more hydrophilic than the disks that were immersed in physiological saline solution (Group 2). The disks that did not have any salt residuals deposited thereon (Group 1) had the highest contact angles and, thus, were the least hydrophilic.

The contact angles and the corresponding hydrophilicity of the disks of Groups 2 and 3 of the present example (having Biomet 3i NanoTite™ surfaces) are comparable to those of the disks of Groups 2 and 3 of Example 2 above (having only Osseotite® surfaces).

Example 4

Since, as demonstrated in Examples 1-3 above, the lactated Ringer's solution salt residuals demonstrated a more robust effect on the initial hydrophilicity of the tested disk surfaces, an experiment was conducted to determine whether all of the constituents of the lactated Ringer's solution were causing the robust effect on hydrophilicity.

Thirty-five titanium 6AL-4V ELI alloy disks were machined using typical turning techniques. After machining, the disks were cleaned with an aqueous detergent including ultraonics to remove residual machining fluid. The disks were then rinsed thoroughly with deionized water and oven dried. After oven drying, the disks were roughened using the dual acid-etched process described in U.S. Pat. App. Pub. No. 2004/0265780, which has been incorporated by reference herein. Discrete crystals of hydroxyapatite were then deposited on the roughened surfaces of the disks using the process described in U.S. Pat. App. Pub. Nos. 2007/0110890 and 2007/0112353, which have been incorporated by reference herein, to produce a Biomet 3i NanoTite™ surface. The disks were then oven dried.

The thirty-five Biomet 3i NanoTite™ titanium 6AL-4V ELI alloy disks were then separated into seven groups that included various concentrations of the components of lactated Ringer's solution. Group 1 included five disks and was utilized as a control group. Group 2 included five disks that were immersed in a solution of about 0.03 w/w % potassium chloride (KCl). Group 3 included five disks that were immersed in a solution of about 0.3 w/w % potassium chloride (KCl). Group 4 included five disks that were immersed in a solution of about 0.02 w/w % calcium chloride ($CaCl_2$). Group 5 included five disks that were immersed in a solution of about 0.2 w/w % calcium chloride ($CaCl_2$). Group 6 included five disks that were immersed in a solution of about 0.3 w/w % sodium lactate ($C_5H_5NaO_3$). Group 7 included five disks that were immersed in a solution of about 3.0 w/w % sodium lactate ($C_5H_5NaO_3$). After each group of disks was soaked in its respective solution for about five minutes, the disks were oven dried utilizing a forced convection oven at 100° C. The disks were then packaged in polyethylene ziplock type bags.

One disk from each of the seven groups was then analyzed using EDS to determine changes in the surface chemistry. The results are summarized in Table 7 below.

TABLE 7

|  | Group 1 Biomet 3i NanoTite™ Control | Group 2 0.03 w/w % KCl | Group 3 0.3 w/w % KCl | Group 4 0.02 w/w % CaCl$_2$ | Group 5 0.2 w/w % CaCl$_2$ | Group 6 0.3 w/w % C$_5$H$_5$NaO$_3$ | Group 7 3 w/w % C$_5$H$_5$NaO$_3$ |
|---|---|---|---|---|---|---|---|
| Titanium | 82.86 | 83.65 | 68.20 | 86.39 | 52.05 | 75.35 | 54.77 |
| Vanadium | 1.64 | 4.31 | 2.88 | 2.41 | 0 | 0 | 1.43 |
| Aluminum | 5.28 | 5.63 | 4.73 | 5.58 | 3.60 | 3.53 | 3.66 |
| Oxygen | 6.90 | 3.59 | 0 | 3.51 | 31.08 | 12.89 | 25.32 |
| Carbon | 1.45 | 0 | 0 | 0 | 0 | 4.27 | 9.56 |
| Calcium | 1.22 | 0.53 | 1.56 | 1.13 | 7.16 | 1.31 | 0.78 |
| Phosphorus | 0.67 | 0.75 | 0.65 | 0 | 0 | 0.38 | 0.24 |
| Sodium | 0 | 0 | 0 | 0 | 0 | 2.28 | 4.26 |
| Chloride | 0 | 0.78 | 10.81 | 1.00 | 6.13 | 0 | 0 |
| Potassium | 0 | 0.77 | 11.20 | 0 | 0 | 0 | 0 |
| Total | 100 | 100 | 100 | 100 | 100 | 100 | 100 |

Figure 12A:
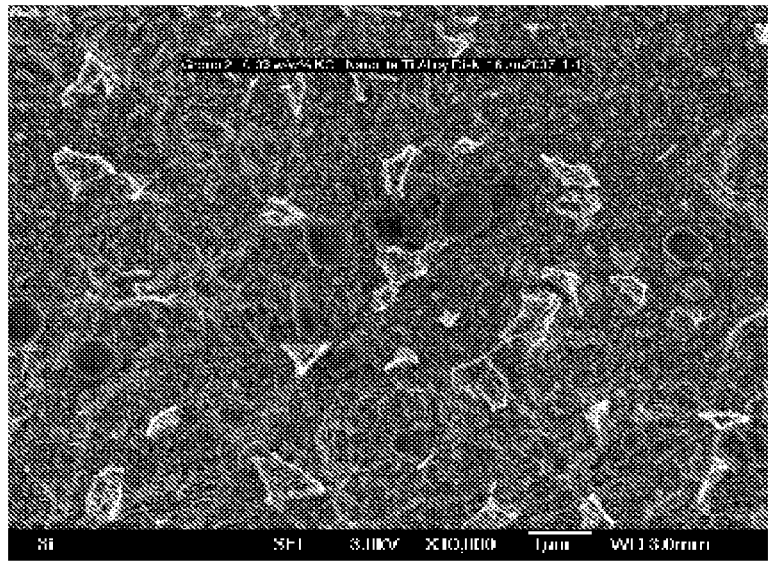
FIG. 12a is an FESEM image showing a dual acid etched titanium alloy disk having hydroxyapatite particles deposited thereon at 10kX after being soaked in a 0.03 w/w % potassium chloride solution.
Figure 12B:
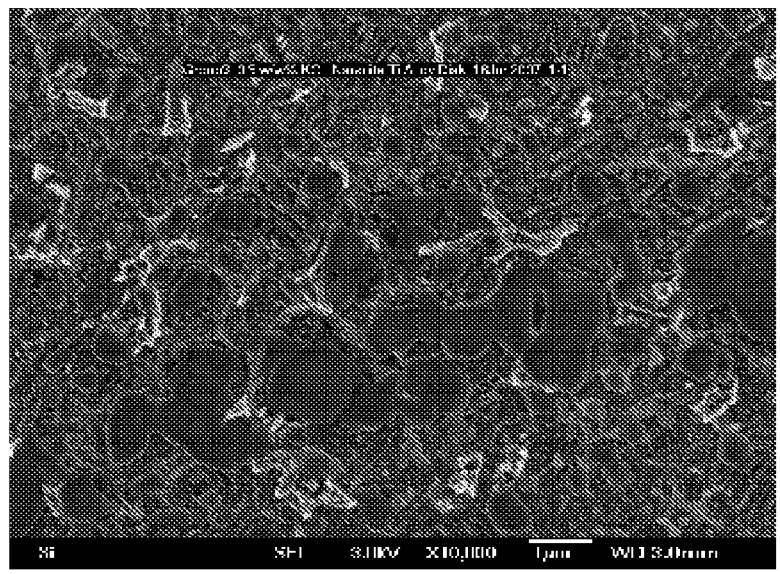
FIG. 12b is an FESEM image showing a dual acid etched titanium alloy disk having hydroxyapatite particles deposited thereon at 10kX after being soaked in a 0.3 w/w % potassium chloride solution.
Figure 12C:
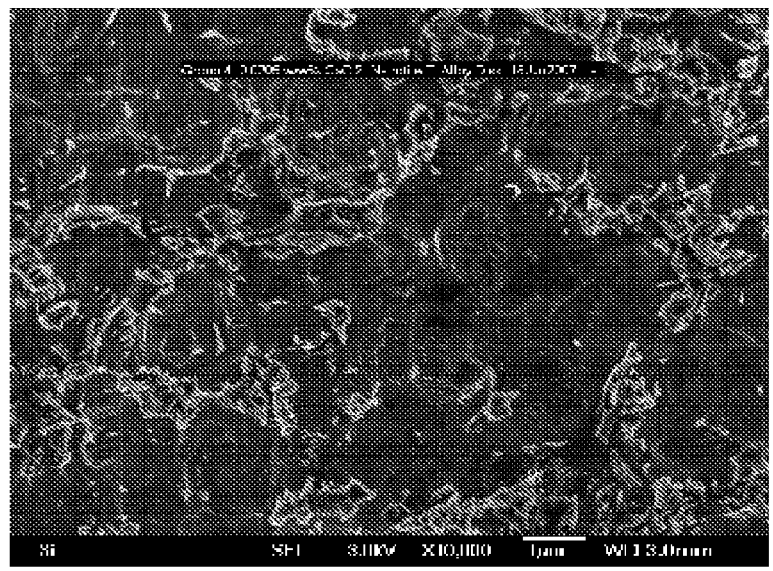
FIG. 12c is an FESEM image showing a dual acid etched titanium alloy disk having hydroxyapatite particles deposited thereon at 10kX after being soaked in a 0.02 w/w % calcium chloride solution.
Figure 12D:
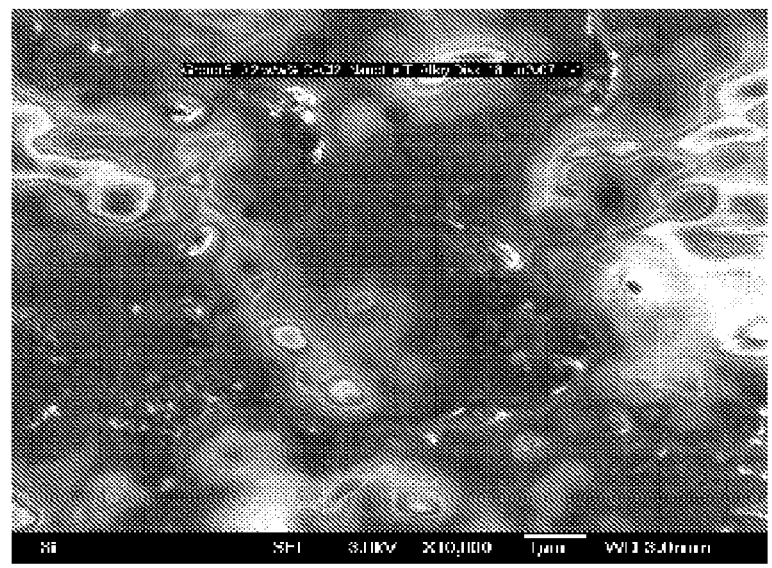
FIG. 12d is an FESEM image showing a dual acid etched titanium alloy disk having hydroxyapatite particles deposited thereon at 10kX after being soaked in a 0.2 w/w % calcium chloride solution.
Figure 12E:
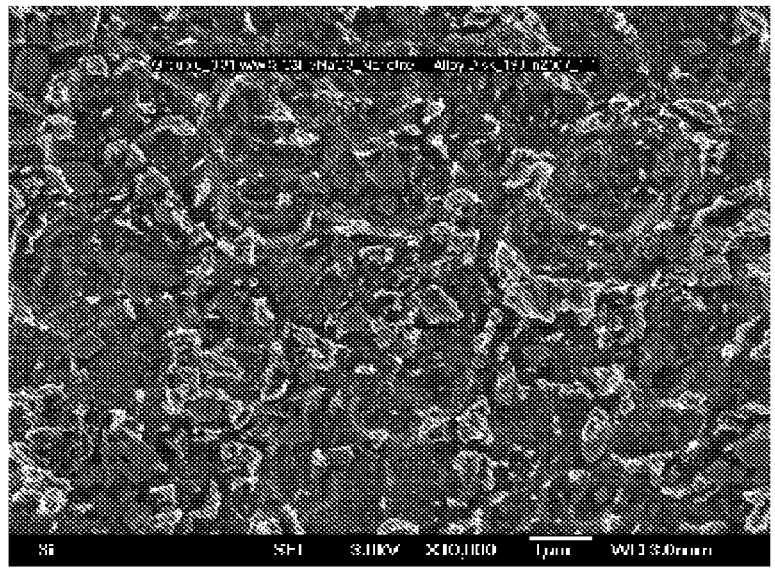
FIG. 12e is an FESEM image showing a dual acid etched titanium alloy disk having hydroxyapatite particles deposited thereon at 10kX after being soaked in a 0.3 w/w % sodium lactate solution.
Figure 12F:
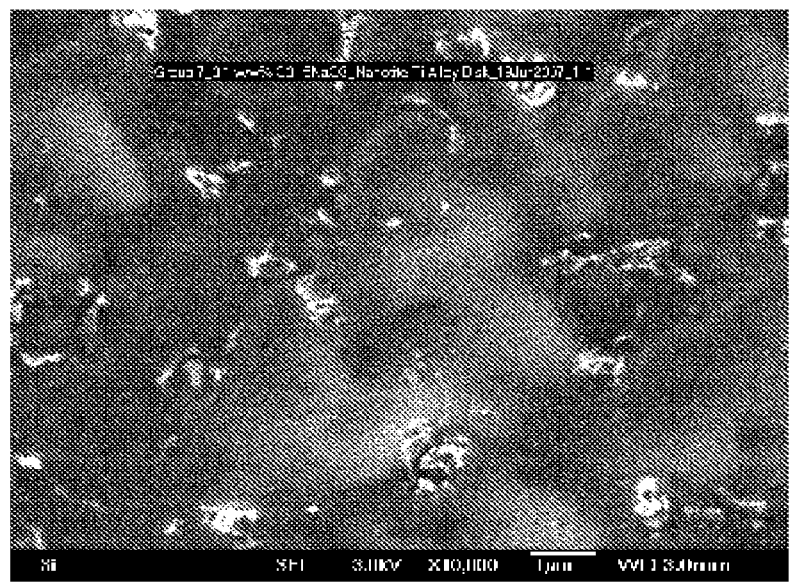
FIG. 12f is an FESEM image showing a dual acid etched titanium alloy disk at 10kX having hydroxyapatite particles deposited thereon after being soaked in a 3.0 w/w % sodium lactate solution.

The same disks were then imaged using an FESEM to show the variations in the surface chemistry of the various disks. FIG. 11a shows the disk from the control group (Group 1), FIG. 12a shows the disk that was immersed in the solution of about 0.03 w/w % KCl (Group 2), FIG. 12b shows the disk that was immersed in the solution of about 0.3 w/w % KCl (Group 3), FIG. 12c shows the disk that was immersed in the solution of about 0.02 w/w % CaCl$_2$ (Group 4), FIG. 12d shows the disk that was immersed in the solution of about 0.2 w/w % CaCl$_2$ (Group 5), FIG. 12e shows the disk that was immersed in the solution of about 0.3 w/w % C$_5$H$_5$NaO$_3$ (Group 6), and FIG. 12f shows the disk that was immersed in the solution of about 3.0 w/w % C$_5$H$_5$NaO$_3$ (Group 7).

Contact angles were then measured on each side of four disks from each group. The results are included in Table 8 below.

TABLE 8

| Sample | Group 1- Biomet 3i NanoTite™ Control | Group 2- 0.03 w/w % KCl | Group 3- 0.3 w/w % KCl | Group 4- 0.02 w/w % CaCl$_2$ | Group 5- 0.2 w/w % CaCl$_2$ | Group 6- 0.31 w/w % C$_5$H$_5$NaO$_3$ | Group 7- 3.1 w/w % C$_5$H$_5$NaO$_3$ |
|---|---|---|---|---|---|---|---|
| 1 | 78 | 80 | 50 | 50 | 10 | 15 | 5 |
| 2 | 81 | 74 | 60 | 41 | 10 | 9 | 5 |
| 3 | 74 | 72 | 63 | 32 | 13 | 10 | 6 |
| 4 | 76 | 65 | 51 | 36 | 13 | 6 | 5 |
| 5 | 85 | 71 | 55 | 42 | 25 | 13 | 6 |
| 6 | 91 | 73 | 55 | 42 | 26 | 10 | 5 |
| 7 | 80 | 73 | 53 | 45 | 17 | 10 | 5 |
| 8 | 78 | 70 | 53 | 46 | 10 | 7 | 5 |
| Mean | 80.38 | 72.25 | 55.00 | 41.75 | 15.50 | 10.00 | 5.25 |
| SD | 5.42 | 4.20 | 4.44 | 5.68 | 6.61 | 2.93 | 0.46 |

As demonstrated in Tables 7 and 8, the results indicated that salt residuals were deposited on all of the disks and that all of the salt residuals tested increased the initial hydrophilicity of the dual acid etched (Osseotite®) and discrete crystal deposited (Biomet 3i NanoTite™) surfaces.

Example 5

The above-described processes deposited salt residuals on a disk surface. These salt residuals are intended to be non-toxic and easily absorbed in aqueous media. The following experiment demonstrates the water soluble nature of the salt residuals.

Four titanium 6AL-4V ELI alloy disks were machined using typical turning techniques. The disks were pre-cleaned with an aqueous detergent including ultraonics to remove residual machining fluid. The disks were then rinsed thoroughly with deionized water and oven dried. After oven drying, the disks were roughened using the dual acid-etched process described in U.S. Pat. App. Pub. No. 2004/0265780, which has been incorporated by reference herein. Discrete crystals of hydroxyapatite were then deposited on the roughened surfaces of the disks using the process described in U.S. Pat. App. Pub. Nos. 2007/0110890 and 2007/0112353, which have been incorporated by reference herein, to produce a Biomet 3i NanoTite™ surface. The disks were then dried.

The four titanium 6AL-4V ELI alloy disks were then separated into two groups. Group 1 included two disks that were immersed in physiological saline for about five minutes and then oven dried utilizing a forced convection oven at a temperature of 100° C. Group 2 included two disks that were immersed in lactated Ringer's solution for about five minutes and then oven dried utilizing a forced convection oven at 100° C.

Figure 13A:
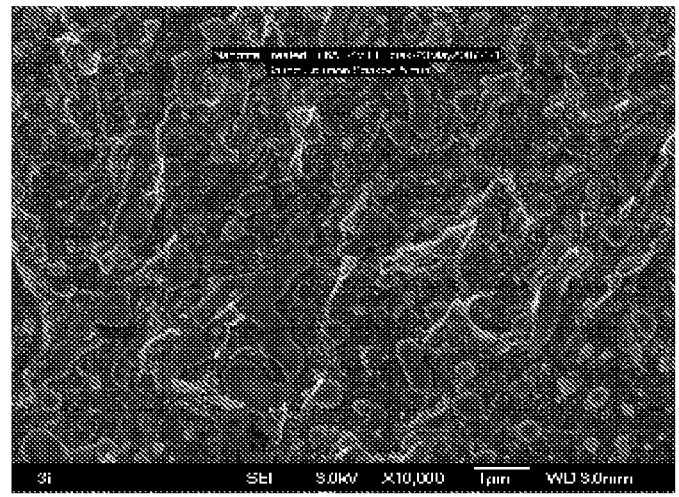
FIG. 13a is an FESEM image showing a dual acid etched titanium alloy disk having hydroxyapatite particles deposited thereon at 10kX after being soaked in physiological saline solution.
Figure 14A:
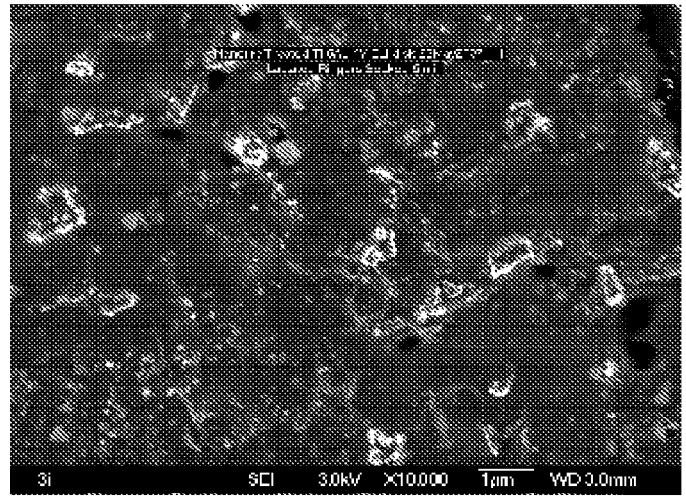
FIG. 14a is an FESEM image showing a dual acid etched titanium alloy disk having hydroxyapatite particles deposited thereon at 10kX after being soaked in lactated Ringer's solution.

The disks were then imaged using an FESEM to show the variations in the surface chemistry of the various disks. FIG. 13a shows the FESEM image of one of the disks of Group 1, and FIG. 14a shows the FESEM image of one of the disks of Group 2. EDS was performed on the surfaces, the results of which are shown in Table 9 below.

Post analysis, the disks from each group were rinsed for 1 minute in stagnant deionized water at a pH ranging from about 6 to about 7.5 at a temperature of about 37° C. (to simulate standard human body temperature). After being rinsed, the disks were oven dried in a forced convection oven set at 100° C. and packaged in polyethylene zip-lock type bags.

Figure 13B:
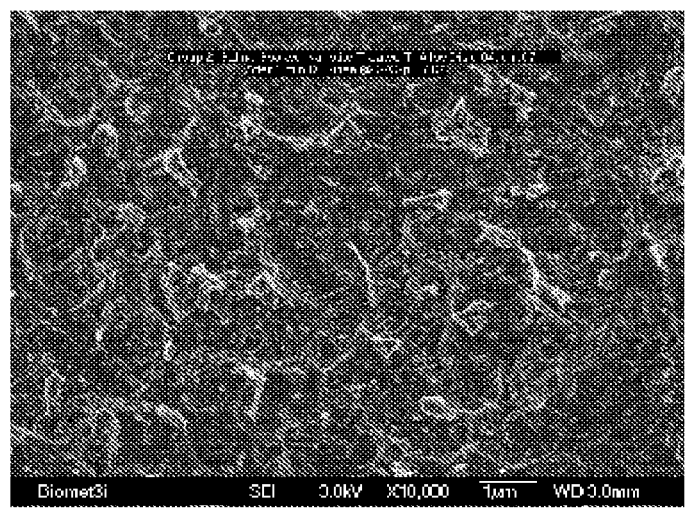
FIG. 13b is an FESEM image showing the disk of FIG. 13a after being rinsed in deionized water and oven dried.
Figure 14B:
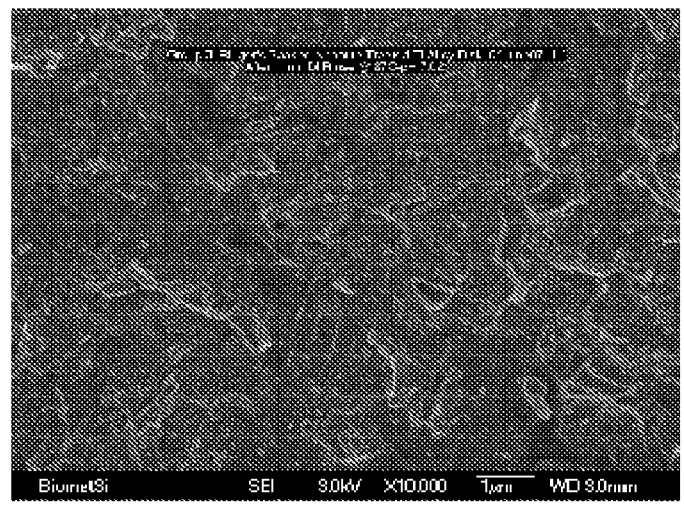
FIG. 14b is an FESEM image showing the disk of FIG. 14a after being rinsed in deionized water and oven dried.

The disks were subsequently re-imaged using an FESEM at 10kX magnification. FIG. 13b shows the FESEM image of the disk of FIG. 13a (Group 1) post-rinsing and drying, and FIG. 14b shows the FESEM image of the disk of FIG. 14a (Group 2) post-rinsing and drying. EDS was also re-performed, the results of which are provided in Table 9 below.

Group 2 included twelve implants that were immersed in lactated Ringer's solution and oven dried utilizing a forced convection oven at 100° C. The implants of Group 2 were then packaged in a nylon bag, appropriately labeled, and sterilized via gamma irradiation. Group 3 included twelve implants that were immersed in a solution including about 0.2 w/w % $CaCl_2$ and oven dried utilizing a forced convection oven at 100° C. The implants of Group 3 were then packaged in a nylon bag, appropriately labeled, and sterilized via gamma irradiation. Lactated Ringer's solution was used to demonstrate the effect of an organic salt (sodium lactate). 0.2 w/w % $CaCl_2$ solution was used to demonstrate the effect of a non-organic salt (calcium chloride). Additionally, the residuals

TABLE 9

|  | Control Group - Biomet 3i NanoTite ™ Control | Group 1 - Physiological Saline (w/w %) | Group 1 - After 1 minute rinse, Physiological Saline (w/w %) | Group 2 - Lactated Ringer's (w/w %) | Group 2 - After 1 minute rinse, Lactated Ringer's (w/w %) |
|---|---|---|---|---|---|
| Titanium | 82.86 | 74.55 | 82.64 | 62.18 | 82.65 |
| Vanadium | 1.64 | 4.06 | 4.33 | 3.52 | 4.31 |
| Aluminum | 5.28 | 5.03 | 5.575 | 4.13 | 5.63 |
| Oxygen | 6.90 | 5.10 | 4.58 | 15.67 | 4.15 |
| Carbon | 1.45 | 1.71 | 1.645 | 5.80 | 2.23 |
| Calcium | 1.22 | 0.71 | 0.875 | 1.08 | 0.76 |
| Phosphorous | 0.67 | 0.31 | 0.36 | 0.15 | 0.30 |
| Sodium | 0 | 4.24 | 0 | 4.17 | 0 |
| Chloride | 0 | 4.32 | 0 | 2.90 | 0 |
| Potassium | 0 | 0 | 0 | 0.41 | 0 |
| Total | 100 | 100 | 100 | 100 | 100 |

The qualitative images from the FESEM and quantitative results from the EDS (see Table 9) indicated that the 1 minute rinse was sufficient to remove the sodium, chloride, potassium, carbon, and oxygen residuals to typical pre-salt deposition levels. Thus, the salt residuals were shown to be water soluble and easily absorbed in aqueous media.

Example 6

The above-described processes deposit non-toxic, soluble salt residues on the surface. The salt residues have been shown to increase the surface hydrophilicity (wettability). The following in-vivo experiment utilizing a rat demonstrates the effect of this surface enhancement and quantifies the strength of the interface between osseointegrated bone and implants including salt residues.

Thirty-six tensile strength titanium 6AL-4V ELI implants (6 mm×4 mm×1.5 mm) were machined using typical turning techniques. After machining, the implants were cleaned with an aqueous detergent including ultraonics to remove residual machining fluid. The implants were then rinsed thoroughly with deionized water and oven dried. After oven drying, the implants were roughened using the dual acid-etched process described in U.S. Pat. App. Pub. No. 2004/0265780, which has been incorporated by reference herein. Discrete crystals of hydroxyapatite were then deposited on the roughened surfaces of the implants using the process described in U.S. Pat. App. Pub. Nos. 2007/0110890 and 2007/0112353, which have been incorporated by reference herein, to produce a Biomet 3i NanoTite™ surface. The disks were then dried.

The thirty-six implants were separated into three groups. Group 1 included twelve implants and was utilized as a control group. The implants of Group 1 underwent no further processing, with the exception of packaging in a nylon bag, appropriate labeling, and sterilizing via gamma irradiation.

from these salts exhibited increased surface wettability in the experiments described above.

The implants were placed antero-posteriorly into the distal metaphyses of both femora of male Wistar rats for nine days. The femora of the sacrificed animals were trimmed to the width of the implant and placed in sucrose buffer. The resulting samples included two cortical arches of bone attached to each implant. For each sample, nylon lines were passed through the marrow spaces between the implant and each cortical arch, and the implant was secured in a vice attached to an Instron® Universal Testing System (model 8501), manufactured by Instron Corporation® (Burlington, Ontario). Each nylon line was then attached to a frame of the Instron® machine and displaced at a crosshead speed of 30 mm/min. The amount of force required to rupture the sample was recorded. For each implant, two force/displacement results were generated, one for each femoral arch (medial and lateral). Thus, since each group included twelve implants, twenty-four force/displacement results were obtained for each group. The results are summarized in Table 10 below.

TABLE 10

|  | Group 1 (control) | Group 2 - Lactated Ringer's solution) | Group 3 - 0.2 w/w % $CaCl_2$) |
|---|---|---|---|
| Mean Force (N) | 12.61 | 14.73 | 11.28 |
| Standard Deviation | 5.37 | 5.07 | 6.34 |

The implants from all three groups integrated well. This demonstrated that the addition of the saline residuals had no significant adverse effects on the integration of the implant with bone. In fact, the data indicated that the implants of Group 2 that were immersed in lactated Ringer's solution required about 17% more bone removal force as compared with the control group (p=0.083).

This in-vivo experiment demonstrated the safety of depositing saline residuals on the surface of implants and the potential benefit of select salts on the rate and extent of osseointegration.

While the present invention has been generally described relative to the part of the implant contacting bone tissue, it is contemplated that the acts of etching, acid etching, roughening, and depositing herein described may be performed on the entire implant.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A method of forming an implant to be implanted into living bone, the method comprising the acts of:
    roughening at least a portion of the implant surface to form a roughened surface; and
    increasing the hydrophilicity of the roughened surface by depositing at least one non-toxic salt residual on the roughened surface, the at least one non-toxic salt residual including sodium lactate.

2. The method of claim 1, further comprising, prior to the act of roughening, grit blasting at least a portion of the implant surface with a grit blast media.

3. The method of claim 2, wherein the grit blast media is a resorbable grit blast media.

4. The method of claim 3, wherein the resorbable grit blast media includes calcium phosphate.

5. A dental implant comprising:
    a head portion having a non-rotational feature;
    a lowermost end opposing the head portion; and
    a threaded bottom portion for engaging bone between the head portion and the lowermost end, the threaded bottom portion having a roughened surface with an array of microscale irregularities, the threaded bottom portion further including at least one non-toxic salt residual located on the roughened surface, the at least one non-toxic salt residual including sodium lactate.

6. The implant of claim 5, wherein the implant is made of a metal selected from the group consisting of titanium and titanium alloys.

7. The dental implant of claim 5, wherein the microscale irregularities have peak-to-valley heights not greater than about 20 microns.

8. The dental implant of claim 5, wherein the at least one non-toxic salt residual is configured to increase the hydrophilicity of the roughened surface.

9. The dental implant of claim 5, wherein the roughened surface further includes discrete nanoparticles comprising a material having a property that promotes osseointegration.

10. The dental implant of claim 9, wherein the nanoparticles are hydroxyapatite nanocrystals.

11. The dental implant of claim 5, wherein a contact angle formed by a deionized water droplet on the surface of the implant ranges from about 5° to about 65°.

12. The dental implant of claim 5, wherein the roughened surface is a grit blasted surface.

13. A dental implant comprising:
    a head portion having a non-rotational feature;
    a lowermost end opposing the head portion; and
    a threaded bottom portion for engaging bone between the head portion and the lowermost end, the threaded bottom portion having a roughened surface with an array of microscale irregularities, the threaded bottom portion further including discrete non-toxic salt residuals located on the roughened surface, the discrete non-toxic salt residuals including sodium lactate.

14. The dental implant of claim 13, wherein the implant is made of titanium or titanium alloy.

15. The dental implant of claim 13, wherein the microscale irregularities have peak-to-valley heights not greater than about 20 microns.

16. The dental implant of claim 13, wherein the discrete non-toxic salt residuals are configured to increase the hydrophilicity of the roughened surface.

17. The dental implant of claim 13, wherein the roughened surface further includes discrete nanoparticles comprising a material having a property that promotes osseointegration.

18. The dental implant of claim 17, wherein the nanoparticles are hydroxyapatite nanocrystals.

19. The dental implant of claim 13, wherein a contact angle formed by a deionized water droplet on the surface of the implant ranges from about 5° to about 65°.

20. The dental implant of claim 13, wherein the roughened surface is a grit blasted surface.

* * * * *